United States Patent
Yu et al.

(10) Patent No.: US 9,835,540 B2
(45) Date of Patent: Dec. 5, 2017

(54) DEVICES AND METHODS FOR MANIPULATING COMPONENTS IN A FLUID SAMPLE

(71) Applicant: Becton, Dickinson and Company, Franklin Lakes, NJ (US)

(72) Inventors: Liping Yu, San Jose, CA (US); Brian David Warner, Martinez, CA (US); Joseph T. Trotter, La Jolla, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 17 days.

(21) Appl. No.: 15/154,810

(22) Filed: May 13, 2016

(65) Prior Publication Data
US 2016/0252445 A1   Sep. 1, 2016

Related U.S. Application Data

(60) Division of application No. 14/590,659, filed on Jan. 6, 2015, now Pat. No. 9,513,205, which is a continuation of application No. 14/061,678, filed on Oct. 23, 2013, now Pat. No. 8,956,536.
(Continued)

(51) Int. Cl.
*G01N 33/487* (2006.01)
*G01N 15/14* (2006.01)
(Continued)

(52) U.S. Cl.
CPC .... *G01N 15/1404* (2013.01); *B01L 3/502761* (2013.01); *B03C 1/02* (2013.01); *B03C 1/288* (2013.01); *G01N 1/34* (2013.01); *G01N 1/4077* (2013.01); *G01N 15/02* (2013.01); *G01N 15/1056* (2013.01); *G01N 15/14* (2013.01);
(Continued)

(58) Field of Classification Search
CPC ............................................... G01N 33/48735
See application file for complete search history.

(56) References Cited

U.S. PATENT DOCUMENTS

| | | |
|---|---|---|
| 4,772,383 A | 9/1988 | Christensen |
| 5,147,562 A | 9/1992 | Heyman |
| 5,411,863 A | 5/1995 | Miltenyi |
| 5,527,460 A | 6/1996 | Trampler et al. |
| 5,541,072 A | 7/1996 | Wang et al. |

(Continued)

FOREIGN PATENT DOCUMENTS

| | | |
|---|---|---|
| GB | 2098498 A | 11/1982 |
| JP | 2006-341202 A | 12/2006 |

(Continued)

OTHER PUBLICATIONS

Demedeiros et al. "Immunostaining Protocols for Flow Cytometric Analysis of Adherent Cells," R&D Systems, Tools for Cell Biology Research, 2009, 2 pages.
(Continued)

*Primary Examiner* — Rosanne Kosson
(74) *Attorney, Agent, or Firm* — Bret E. Field; Bozicevic, Field & Francis LLP

(57) ABSTRACT

Devices for sorting components (e.g., cells) contained in a liquid sample are provided. In certain aspects, the devices include a magnetic separation device and an acoustic concentrator device fluidically coupled to magnetic separation device. Aspects of the invention further include methods for sorting cells in a liquid sample, and systems, and kits for practicing the subject methods.

10 Claims, 17 Drawing Sheets

Related U.S. Application Data

(60) Provisional application No. 61/719,062, filed on Oct. 26, 2012.

(51) Int. Cl.
   *G01N 1/34* (2006.01)
   *G01N 33/543* (2006.01)
   *B03C 1/28* (2006.01)
   *G01N 15/02* (2006.01)
   *B01L 3/00* (2006.01)
   *G01N 1/40* (2006.01)
   *B03C 1/02* (2006.01)
   *G01N 15/10* (2006.01)
   *G01N 15/00* (2006.01)

(52) U.S. Cl.
   CPC ... *G01N 15/1425* (2013.01); *G01N 33/54326* (2013.01); *B01L 2200/0652* (2013.01); *B01L 2300/0877* (2013.01); *B01L 2400/043* (2013.01); *B01L 2400/0439* (2013.01); *B03C 2201/18* (2013.01); *B03C 2201/26* (2013.01); *G01N 15/1459* (2013.01); *G01N 2001/4038* (2013.01); *G01N 2001/4094* (2013.01); *G01N 2015/008* (2013.01); *G01N 2015/0288* (2013.01); *G01N 2015/1006* (2013.01); *G01N 2015/142* (2013.01); *G01N 2015/149* (2013.01)

(56) References Cited

U.S. PATENT DOCUMENTS

| | | |
|---|---|---|
| 5,622,831 A | 4/1997 | Liberti et al. |
| 5,626,767 A | 5/1997 | Trampler et al. |
| 5,665,605 A | 9/1997 | Coakley et al. |
| 5,688,405 A | 11/1997 | Dickinson et al. |
| 5,688,406 A | 11/1997 | Dickinson et al. |
| 5,770,388 A | 6/1998 | Vorpahl |
| 5,795,470 A | 8/1998 | Wang et al. |
| 5,837,200 A | 11/1998 | Diessel et al. |
| 5,868,255 A | 2/1999 | McGaa |
| 5,876,593 A | 3/1999 | Liberti et al. |
| 5,902,489 A | 5/1999 | Yasuda et al. |
| 5,912,182 A | 6/1999 | Coakley et al. |
| 5,918,272 A | 6/1999 | Snyder et al. |
| 5,945,281 A | 8/1999 | Prabhu |
| 5,968,820 A | 10/1999 | Zborowski et al. |
| 5,985,153 A | 10/1999 | Dolan et al. |
| 5,976,369 A | 11/1999 | Howe et al. |
| 5,979,664 A | 11/1999 | Brodeur |
| 6,013,188 A | 1/2000 | Terstappen et al. |
| 6,013,532 A | 1/2000 | Liberti et al. |
| 6,036,027 A | 3/2000 | Grimes |
| 6,120,735 A | 9/2000 | Zborowski et al. |
| 6,126,835 A | 10/2000 | Barbera-Guillem et al. |
| 6,136,182 A | 10/2000 | Dolan et al. |
| 6,216,538 B1 | 4/2001 | Yasuda et al. |
| 6,241,894 B1 | 6/2001 | Briggs et al. |
| 6,254,830 B1 | 7/2001 | Pivarnik et al. |
| 6,273,262 B1 | 8/2001 | Yasuda et al. |
| 6,280,618 B2 | 8/2001 | Watkins et al. |
| 6,297,061 B1 | 10/2001 | Wu et al. |
| 6,332,541 B1 | 12/2001 | Coakley et al. |
| 6,361,749 B1 | 3/2002 | Terstappen et al. |
| 6,432,630 B1 | 8/2002 | Blankenstein |
| 6,467,350 B1 | 10/2002 | Kaduchak et al. |
| 6,467,630 B1 | 10/2002 | Zborowski et al. |
| 6,613,525 B2 | 9/2003 | Nelson et al. |
| 6,623,982 B1 | 9/2003 | Liberti et al. |
| 6,630,355 B1 | 10/2003 | Pivarnik et al. |
| 6,644,118 B2 | 11/2003 | Kaduchak et al. |
| 6,645,777 B1 | 11/2003 | Letcher et al. |
| 6,660,159 B1 | 12/2003 | Terstappen et al. |
| 6,699,711 B1 | 3/2004 | Hahn et al. |
| 6,749,666 B2 | 6/2004 | Meegan, Jr. |
| 6,790,366 B2 | 9/2004 | Terstappen et al. |
| 6,797,514 B2 | 9/2004 | Berenson et al. |
| 6,809,315 B2 | 10/2004 | Ellson et al. |
| 6,854,338 B2 | 2/2005 | Khuri-Yakub et al. |
| 6,858,440 B1 | 2/2005 | Letcher et al. |
| 6,890,426 B2 | 5/2005 | Terstappen et al. |
| 6,929,750 B2 | 8/2005 | Laurell et al. |
| 6,932,097 B2 | 8/2005 | Ellson et al. |
| 7,022,505 B2 | 4/2006 | Chandler et al. |
| 7,033,473 B2 | 4/2006 | Gascoyne et al. |
| 7,056,657 B2 | 6/2006 | Terstappen et al. |
| 7,108,137 B2 | 9/2006 | Lal et al. |
| 7,138,269 B2 | 11/2006 | Blankenstein |
| 7,150,779 B2 | 12/2006 | Meegan, Jr. |
| 7,232,691 B2 | 6/2007 | Kraus, Jr. et al. |
| 7,340,957 B2 | 3/2008 | Kaduchak et al. |
| 7,373,805 B2 | 5/2008 | Hawkes et al. |
| 7,484,414 B2 | 2/2009 | Priev et al. |
| 7,521,023 B2 | 4/2009 | Laugharn, Jr. et al. |
| 7,666,308 B2 | 2/2010 | Scholtens et al. |
| 7,670,558 B2 | 3/2010 | Katou et al. |
| 7,674,630 B2 | 3/2010 | Siversson |
| 7,722,815 B2 | 5/2010 | Katou et al. |
| 7,807,454 B2 | 10/2010 | Oh et al. |
| 7,837,040 B2 | 11/2010 | Ward et al. |
| 7,846,382 B2 | 12/2010 | Strand et al. |
| 7,980,752 B2 | 7/2011 | Sarvazyan |
| 7,998,696 B2 | 8/2011 | Zaugg et al. |
| 8,071,054 B2 | 12/2011 | Oh et al. |
| 8,071,395 B2 | 12/2011 | Davis et al. |
| 8,083,068 B2 | 12/2011 | Kaduchak et al. |
| 8,134,705 B2 | 3/2012 | Kaduchak et al. |
| 8,166,819 B2 | 5/2012 | Wanis et al. |
| 8,227,257 B2 | 7/2012 | Ward et al. |
| 8,263,387 B2 | 9/2012 | Pagano et al. |
| 8,263,407 B2 | 9/2012 | Goddard et al. |
| 8,266,950 B2 | 9/2012 | Kaduchak et al. |
| 8,266,951 B2 | 9/2012 | Kaduchak et al. |
| 8,277,764 B2 | 10/2012 | Gilbert et al. |
| 8,292,083 B2 | 10/2012 | Varghese et al. |
| 8,300,303 B1 | 10/2012 | Ruffa |
| 8,309,408 B2 | 11/2012 | Ward et al. |
| 8,323,568 B2 | 12/2012 | McBrady et al. |
| 8,372,590 B2 | 2/2013 | Bernard et al. |
| 8,409,415 B2 | 4/2013 | Liu et al. |
| 8,436,993 B2 | 5/2013 | Kaduchak et al. |
| 8,956,536 B2 | 2/2015 | Yu et al. |
| 2004/0264293 A1 | 12/2004 | Laugharn, Jr. et al. |
| 2006/0226924 A1 | 10/2006 | Chen et al. |
| 2009/0042310 A1* | 2/2009 | Ward .............. G01N 15/1404 436/154 |
| 2009/0194420 A1 | 8/2009 | Mariella, Jr. et al. |
| 2009/0317884 A1 | 12/2009 | Laugharn, Jr. |
| 2010/0009333 A1 | 1/2010 | Auer |
| 2011/0137018 A1 | 6/2011 | Chang-Yen et al. |
| 2012/0304749 A1 | 12/2012 | Kaduchak et al. |
| 2013/0116459 A1 | 5/2013 | Marrone et al. |

FOREIGN PATENT DOCUMENTS

| | | |
|---|---|---|
| JP | 2011-185839 A | 9/2011 |
| WO | WO 2008/010111 A2 | 1/2008 |
| WO | WO 2008/147530 A1 | 12/2008 |
| WO | 2009132151 A2 | 10/2009 |
| WO | WO 2012/148648 A2 | 11/2012 |
| WO | WO 2013/095867 A1 | 6/2013 |

OTHER PUBLICATIONS

Adams et al. "Integrated acoustic and magnetic separation in microfluidic channels", Applied Physics Letters 95, 254103 (2009), 3 pages.

Evander et al. "Acoustophoresis in Wet-Etched Glass Chips", Anal. Chem. 80, pp. 5178-5185 (2008).

Iacob et al., "High Gradient Magnetic Separation Ordered Matrices", European Cells and Materials, vol. 3, Suppl. 2, pp. 167-169 (2002).

(56) References Cited

OTHER PUBLICATIONS

Laurell et al. "Chip integrated strategies for acoustic separation and manipulation of cells and particles", Chem. Soc. Rev., 36, pp. 492-506 (2007).
Lenshof et al. "Acoustophoretic Pretreatment of Cell Lysate Prior to FACS Analysis", MicroTAS 2010, Oct. 3-7, 2010, Groningen, The Netherlands, pp. 1577-1579.
Petersson et al. "Free Flow Acoustophoresis: Microfluidic-Based Mode of Particle and Cell Separation", Anal. Chem. 79 (14), pp. 5117-5123 (2007).
Sandin et al., "Magnetophoresis and cytometry with magnetic microparticles", International Congress Series, vol. 1300, pp. 271-274, (2007).
Warner et al. "Improving Flow Cytometric Performance Using Modular In-Line Acoustophoretic Washing of Lysed Blood Samples", Cyto2012, Leipzig, Germany, Jun. 23-27, 2012, 4 pgs.
Warner et al. Accelerated Cell Sorting Using In-Line Sample Pre-Enrichment. Cyto2013, San Diego, CA, USA, May 19-22, 2013, 2 pgs.
Warner et al. "An In-Line Sample Enrichment Modular Tool for Flow Cytometry", Cyto2012, Leipzig, Germany, Jun. 23-27, 2012, 1 page.
Machine translation of specification of Nokodai TLO KK, JP 2011-185839 A, 2011.
English translation of bibliographic information of Nokodai TLO KK, JP 2011-185839 A, 2011.
Marentis et al. "Microfluidic sonicator for real-time disruption of eukaryotic cells and bacterial spores for DNA analysis," Ultrasound in Medicine and Biology, New York, NY, US, vol. 31, No. 9, Sep. 1, 2005, pp. 1265-1277.

\* cited by examiner

DEVICES AND METHODS FOR MANIPULATING COMPONENTS IN A FLUID SAMPLE

INTRODUCTION

Flow cytometry is a well-accepted tool in research that allows a user to rapidly analyze and sort components in a sample fluid. Flow cytometers use a carrier fluid (e.g., a sheath fluid) to pass the sample components, substantially one at a time, through a zone of illumination. Each sample component is illuminated by a light source, such as a laser, and light scattered by each sample component is detected and analyzed. The sample components can be separated based on their optical and other characteristics as they exit the zone of illumination.

Flow cytometry is often used to sort and collect cells for experiments, such as in vivo transplantation and in vitro cell culture. For example, flow cytometry may be used to isolate tumor-free populations of stem cells (e.g., hematopoietic stem cells) for cancer patients undergoing stem cell transplantation. Flow cytometric methods are also increasingly used in disease diagnosis and monitoring, such as for prenatal and neonatal diagnosis of immunological abnormalities. Many applications of flow cytometry demand that cells be analyzed, sorted, or collected at high speed so as to minimize the damage, death, or aggregation of the cells. Further, high efficiency may be required to produce accurate diagnoses.

In certain applications, flow cytometric methods have incorporated a step of magnetic separation of cells. Magnetic separation of cells flowing through a tube or cartridge positioned in an appropriately configured magnetic separation device has been shown to be very convenient. In magnetic separation devices, a sample fluid that includes magnetically labeled components flows through a tube positioned in a magnetic separation device, which includes a magnet. As the sample flows through the tube, magnetically labeled components in the sample are retained in the tube by the magnetic field produced by the magnet. Unlabeled components (e.g., cells) are not retained in the tube and flow through the magnetic separation device.

The cells that flow through the magnetic separation device often must be washed and concentrated prior to use. Often this entails a manual step involving centrifugation, which may be time consuming, damage the cells, or lead to aggregation of the cells in the sample. Further, because the cells often must sit for extended periods of time, the likelihood that the cells form aggregates is high.

SUMMARY

Devices for manipulating components (e.g., cells) contained in a liquid sample are provided. In certain aspects, the devices include a magnetic separation device and an acoustic concentrator device fluidically coupled to magnetic separation device. Aspects of the invention further include methods for sorting cells in a liquid sample, and systems, and kits for practicing the subject methods.

Embodiments of the present disclosure achieve high efficiency, high flow rate and low cost separation of components in a liquid sample. In certain aspects, the components are cells. Cells of interest include, but are not limited to, prokaryotic cells (e.g., bacterial cells or archaeal cells) and eukaryotic cells (e.g. mammalian cells, such as nerve cells, muscle cells, epithelial cells (e.g., circulating tumor cells), stem cells (e.g., hematopoietic stem cells), adipocyte cells and the like). Cells may be detected from a range of samples, including samples obtained from an in vitro source (e.g., a suspension of cells from laboratory cells grown in culture) or from an in vivo source (e.g., a mammalian subject, a human subject, etc.).

In certain aspects, components (e.g., cells) are sorted in a liquid sample using a device that includes a magnetic separation device, and an acoustic concentrator device fluidically coupled to the magnetic separation device. A broad range of magnetic separation devices and acoustic concentrator devices may be included in the subject devices and systems, e.g., as described herein. In certain aspects, a magnetic separation device includes one or more magnetic field sources, such as 2 or more, including 3 or more, 4 or more, or 5 or more. A magnetic separation device may include 1 or more magnetic field guides, such as 2 or more, including 3 or more, 4 or more, or 5 or more. Magnetic field guides of interest include, but are not limited to, magnetic field guides having tapered (e.g., apex) edges, which are configured to increase a magnetic flux from a magnetic field source.

Moreover, a broad range of acoustic concentrator devices may be included in the subject devices and systems, varying in some embodiments in terms of scale (e.g., macro- or micro-scale); chip material (e.g., silicon, glass, etc.); chip dimensions; number of separation channels (e.g., 1 or more, 2 or more, 5 or more, 10 or more, 20 or more, etc.); orientation of the separation channels (e.g., serial, parallel, and/or both); dimensions of the separation channel(s); number of inputs and outputs; type of vibration generator (e.g., a piezoceramic transducer, such as lead zirconate titanate (PZT)); number of vibration generators; wave frequency; voltage applied to the vibration generator; flow rate (e.g., about 1 µl/min, about 100 µl/min, about 1 ml/min, or about 100 ml/min or more); presence or absence of pumps or valves (e.g., one or more syringe pumps, elastomeric pumps, and/or peristaltic pumps); and the like, as shall be described more fully herein. Further, acoustic concentrator devices of interest include, but are not limited to, those as described in U.S. Pat. No. 6,929,750; Laurell, et al. (2007) Chem. Soc. Rev., 2007, 36, 492-606; Petersson, et al. (2005) Analytical Chemistry 77: 1216-1221; and Augustsson, et al. (2009) Lab on a Chip 9: 810-818; the disclosures of which are incorporated herein by reference.

Devices and systems of the present disclosure may include one or more processors configured to control the device or system. In certain aspects, a processor may be configured to apply a magnetic field in a magnetic separation device. A processor may also, or instead, be configured to control an acoustic concentrator device, such as by altering one or more of the shape, frequency and power of the electrical energy delivered to the vibration generator. Aspects of the present disclosure further include closed-loop devices and systems.

Also provided by the present disclosure are methods for manipulating components in a liquid sample. In certain embodiments, the methods include separating magnetically labeled moieties from non-magnetically labeled moieties in the sample, thereby creating a first sorted sample, and acoustically concentrating the first sorted sample to produce a second sorted sample. In certain aspects, the methods further include collecting the second sorted sample, and/or analyzing the sorted sample. Also provided are kits for practicing the subject methods.

BRIEF DESCRIPTION OF THE DRAWINGS

The invention may be best understood from the following detailed description when read in conjunction with the accompanying drawings. Included in the drawings are the following figures:

FIG. 3, Panel b is a diagram depicting a configuration of a plurality of flow channels positioned between a pair of wedge-shaped magnetic field guides in a magnetic separation device according to certain embodiments of the present disclosure. Two flow channels are positioned proximal to the apex of the wedge-shaped magnetic field guides. FIG. 3, Panel c is a diagram depicting another configuration of a plurality of flow channels positioned between a pair of wedge-shaped magnetic field guides in a magnetic separation device according to certain embodiments of the present disclosure. In these embodiments, the two flow channels positioned proximal to the apex of the wedge-shaped magnetic field guides may be formed by creating and inflating a hollow pathway through a pair of press sealed sheets.

FIG. 4, Panel b is a diagram depicting another configuration of a plurality of flow channels positioned between a wedge-shaped magnetic field guide and a flat-edge magnetic field guide in a magnetic separation device according to certain embodiments of the present disclosure. In these embodiments, the flow channels may be formed (like the flow channels described in FIG. 3, Panel c, above) by creating and inflating a hollow pathway through a pair of press sealed sheets.

FIG. 5, Panel b is a diagram depicting another configuration of a plurality of flow paths positioned between a wedge-shaped magnetic field guide and a curved-edge magnetic field guide in a magnetic separation device according to certain embodiments of the present disclosure. In these embodiments, the flow paths may be formed (like the flow channels described in FIG. 3, Panel c, and FIG. 4, Panel b, above) by creating and inflating a hollow pathway through a pair of press sealed sheets.

FIG. 6 depicts a pair of permanent magnetics each coupled to a magnetic field guide having a multiple wedge configuration. In these embodiments, one or more flow channels may be positioned between the multiple wedge-shaped magnetic field guides.

FIG. 7 depicts a single permanent magnetic coupled to two magnetic field guides having a multiple wedge configuration. In these embodiments, one or more flow paths may be positioned between the multiple wedge-shaped magnetic field guides.

DETAILED DESCRIPTION

Figure 1:
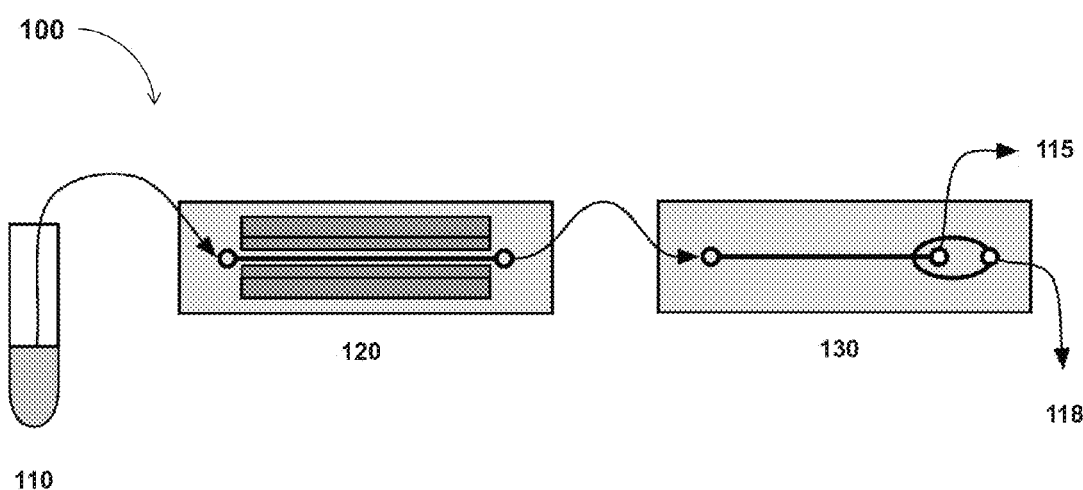
FIG. 1 is a schematic of a system including a magnetic separation device and an acoustic concentrator device fluidically coupled to the magnetic separation device, according to embodiments of the present disclosure.

Devices for manipulating components (e.g., cells) contained in a liquid sample are provided. In certain aspects, the devices include a magnetic separation device and an acoustic concentrator device fluidically coupled to magnetic separation device. Aspects of the invention further include methods for sorting cells in a liquid sample, and systems, and kits for practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Devices

As described above, the present disclosure provides devices for sorting components, such as cells, that are contained in a liquid sample. In certain aspects, the devices include a magnetic separation device and an acoustic concentrator device fluidically coupled to magnetic separation device.

The terms "sample," "liquid sample," and "fluid sample," as used herein means any sample containing one or more individual components in suspension at any desired concentration. For example, the sample can contain $10^{11}$ or less, $10^{10}$ or less, $10^9$ or less, $10^8$ or less, $10^7$ or less, $10^6$ or less, $10^5$ or less, $10^4$ or less, $10^3$ or less, 500 or less, 100 or less, 10 or less, or one component (e.g., cell) per milliliter. The sample can contain a known number of components or an unknown number of components.

Samples may exhibit a wide range of viscosities. The viscosity of a liquid may depend on temperature. In certain embodiments, a fluid sample has a viscosity substantially equal to that of water at the given temperature (e.g., about 1 cP at 20° C., about 0.65 cP at 40° C.). Fluid samples useful in the present disclosure may exhibit a wide range of viscosities, ranging in some aspects from about 0.01 cP to about 750 cP, including about 0.1 cP to about 100 cP, such as about 0.1 cP to 50 cP, about 0.2 cP to about 10 cP, about 0.2 cP to about 2.0 cP, about 0.5 to 1.5 cP, or about 0.75 cP to 1.5 cP.

In certain embodiments, the fluidic sample contains organic (e.g., biological) material. Organic material may be biological or non-biological in origin. A fluidic sample may, in some aspects, contain only organic material. In certain aspects, a sample contains non-organic material. Non-organic material may be chemical (e.g., synthetic) in origin. In certain embodiments, a sample contains both organic and non-organic material.

In certain aspects, the fluidic sample contains cells. Suitable cells include eukaryotic cells (e.g., mammalian cells) and/or prokaryotic cells (e.g., bacterial cells or archaeal cells). Samples may be obtained from an in vitro source (e.g., a suspension of cells from laboratory cells grown in culture) or from an in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic cellular samples.

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

A subject device may be configured as a flow-through device for analyzing liquid samples. By "flow-through" is meant that a liquid sample may enter the device through an inlet, be carried through the device in a flow path, such as a conduit, and then exit the device through an outlet. The device may be configured to carry a continuous stream of the sample through the device and continuously separate magnetically labeled moieties in the sample as the sample flows through the device, and/or continuously separate particles (e.g., cells) based on the acoustic contrast factors (also called an φ-factor; described below) of the particles as the sample flows through the acoustic concentrator portion of the device. Each of the magnetic separation device and the acoustic concentration device may have 1 or more inlets and outlets as desired. For example, each of the magnetic separation device and the acoustic concentrator device may individually include 1 or more inlets, such as 2 or more inlets, such as 3 or more inlets and including 5 or more inlets. In certain embodiments, each of the magnetic separation device and the acoustic concentrator device individually include between 1 and 5 inlets, such as between 2 and 4 inlets and including 3 inlets. Likewise, each of the magnetic separation device and the acoustic concentrator device may individually include 1 or more outlets, such as 2 or more outlets, such as 3 or more outlets and including 5 or more outlets. In certain embodiments, each of the magnetic separation device and the acoustic concentrator device individually include between 1 and 5 outlets, such as between 2 and 4 outlets and including 3 outlets.

The number of inlets and outlets may be the same or different for each of the magnetic separation device and the acoustic concentrator device. For example, in one instance the subject device includes a magnetic separation device which has 1 inlet and 1 outlet and an acoustic concentrator device which has 3 inlets and 3 outlets. In another embodiment, the subject device includes a magnetic separation device which has 1 inlet and 2 outlets and an acoustic concentrator device which has 2 inlets and 2 outlets.

Each of the inlets may be configured for introducing any component into the subject devices, such as for example a fluidic sample, magnetic particles, reagents, solvents and buffers. Where the device includes more than one inlet, each inlet may be employed to introduce the same or different components. For example, one inlet may be employed to introduce fluidic sample while one or more alternate inlets may be employed for introducing a wash buffer or sheath fluid. Each desired component may be introduced into the inlet manually (e.g., by syringe or syringe pump) or by one or more injectors (e.g., computer controlled injection systems, peristaltic pump systems, etc.).

The flow rate through each of the magnetic separation device and the acoustic concentrator device may vary depending on the desired separation, concentration or subsequent analysis in fluid communication with the subject devices, as described in greater detail below. In certain embodiments, the device is configured to have a flow rate of about 1 μL/min or more, such as about 10 μL/min or more, including about 30 μL/min or more, or about 40 μL/min or more, or about 50 μL/min or more, or about 60 μL/min or more, or about 80 μL/min or more, or about 100 μL/min or more, or about 200 μL/min or more, or about 300 μL/min or more, or about 400 μL/min or more, or about 500 μL/min or more, or about 750 μL/min or more, or about 1 mL/min or more, or about 2 mL/min or more, or about 5 mL/min or more, or about 10 mL/min or more, or about 100 mL/min to about 1 L/min. In certain aspects, the flow rate of the device is such that the output from the device is optimal for subsequent analysis using a flow cytometer, such as about 20 to 150 μL/min, including about 30 to 100 μL/min, such as about 40-60 μL/min.

The subject devices may be configured to provide a constant flow rate. By "constant flow rate" is meant that the rate of fluid flow through the subject device increases or decreases by 2% or less, such as by 1.5% or less, such as by 1% or less, such as 0.5% or less, such as 0.5% or less and including changes by 0.1% or less. In some instances, the subject device is configured to provide a constant flow rate of the sample through both the magnetic separation device and the acoustic concentration device. In other instances, the subject device is configured to provide a constant flow rate through only the magnetic separation device. In yet other instances, the subject device is configured to provide a constant flow rate only through the acoustic concentrator device. The flow rate through each of the magnetic separation device and the acoustic concentrator device may be the same or different as desired. In some embodiments, the flow rate through the magnetic separation device is the same as the flow rate through the acoustic concentrator device. In other embodiments, the flow rate through the magnetic separation device is different that the flow rate through the acoustic concentrator device. For example, in certain instances the flow rate through the magnetic separator device is greater than the flow rate through the acoustic concentrator device. In other instances, the flow rate through the magnetic separator device is less than the flow rate through the acoustic concentrator device.

In certain embodiments, flow through the magnetic separator device is substantially free of laminar flow. By substantially free of laminar flow is meant that fluidic flow through the conduit of the magnetic separator device is characterized by a single flow stream and is absent any laminating flow streams. As such, in these embodiments, fluidic sample is flowed through the magnetic separation device in the absence of laminating sheath fluids.

In certain instances, the fluid dynamics of fluidic flow through the magnetic separator device is characterized by substantially turbulent flow. The term "turbulent flow" is used in its conventional sense to mean that fluid flow is a single flow which does not include any laminating flow such as laminar wash buffer flow.

In some embodiments, fluidic flow through the acoustic concentrator device is laminar. The term "laminar flow" is used in its conventional sense to refer to the flow dynamic where fluid flows in a plurality of parallel layers which little to no disruption between the layers. For instance, a stream of sheath buffer may be laminated between two streams of sample in the flow through the acoustic concentrator device. In these embodiments, when an acoustic field is applied, whole cells (e.g., lymphocytes) or particles of higher density are forced radially to a node of the acoustic standing wave in a laminate of flowing wash buffer. The concentrated sample may exit the acoustic concentrator device through a dedicated sample outlet while particles in parallel laminating sample streams may be directed to distinct, separate outlets.

In certain embodiments, the flow rate of the device may be adjusted such that the output from the device is optimal for subsequent analysis by a particular device, such as a BD Biosciences Influx™ cell sorter.

A subject device may facilitate the production of liquid samples that exhibit low entrainment. Entrainment is a measure of the degree of aggregation of components (e.g. cells) in a liquid sample, defined as the ratio of the observed distribution of the component over the expected distribution based on a normal Poisson distribution. In certain aspects, the subject device may facilitate the production of samples with an entrainment factor of 2.0 to 0.0, such as about 1.5 to 0.0, including about 1.0 to 0.0, about 0.75 to 0.0, about 0.5 to 0.0, about 0.4 to about 0.02, or about 0.25 to 0.0.

FIG. 1 shows a schematic of a flow-through fluidic device 100 for manipulating components in a liquid sample according to embodiments of the present disclosure. A liquid sample 110 may be flowed through a subject device that includes a magnetic separation device 120. In certain aspects, a magnetic reagent is added to the liquid sample prior to being flowed through the magnetic separation device 120. As the liquid sample is flowed through the magnetic separation device 120 (e.g., at a rate of about 200-400 μl/min), those components of the liquid sample that have been labeled with a magnetically labeled moiety are retained by the device 120. The output of magnetic separation device may be fluidically coupled and/or in fluidic communication with an acoustic concentrator device 130. The acoustic concentrator device 130 may sort and/or concentrate the fluid sample, thereby producing a sorted sample 115. Fluidic sample emanating from flow-through fluidic device 100 may be collected as waste 118. In certain aspects, the sorted sample 115 may be further analyzed (e.g., such as by flow cytometrically assaying the sorted sample), as shall be described more fully herein.

In some embodiments of the present disclosure, the subject devices contain at least one magnetic separation device and at least one acoustic concentrator device. As such, the subject device includes at least one distinct magnetic separation device module and at least one distinct acoustic concentrator device module. In certain aspects, the subject devices do not include a co-located magnetic field source and an acoustic concentrator source positioned proximal to a common sample chamber or vessel.

In these embodiments, the subject devices may contain two or more magnetic separation devices, such as 3 or more, including 4 or more, 5 or more, 6 or more, or 7 to 10. When a subject device contains 2 or more magnetic separation devices, the magnetic separation devices may be arranged in any convenient configuration, such as in a serial configuration, parallel configuration, or a combination of the two. Moreover, when a subject device contains 2 or more magnetic separation devices, the magnetic separation devices may be substantially identical, identical, or heterogeneous (i.e., differ in one or more ways, such as in the number and/or type(s) of magnet(s), number and/or type(s) of magnetic field guide(s), dimensions of the magnets, etc.)

In some embodiments, the subject devices may contain two or more acoustic concentrator devices, such as 3 or more, including 4 or more, 5 or more, 6 or more, or 7 to 10. When a subject device contains 2 or more acoustic concentrator devices, the acoustic concentrator devices may be arranged in any convenient configuration, such as in a serial configuration, parallel configuration, or a combination of the two. Moreover, when a subject device contains 2 or more acoustic concentrator devices, the acoustic concentrator devices may be substantially identical, identical, or heterogeneous (e.g., differ in one or more ways, such as in the dimensions of the flow channel, the applied voltage, the oscillation frequency, etc.).

Figure 2:
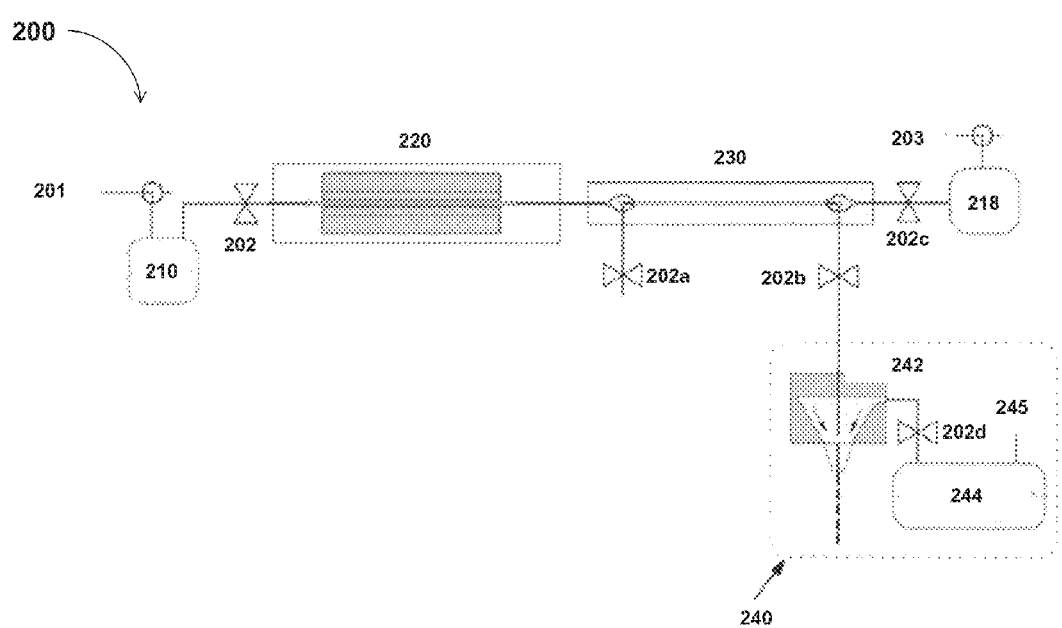
FIG. 2 is a fluidic configuration diagram of a system including a magnetic separation device, an acoustic concentrator device, and a flow cytometer, according to embodiments of the present disclosure.
Figure 10:
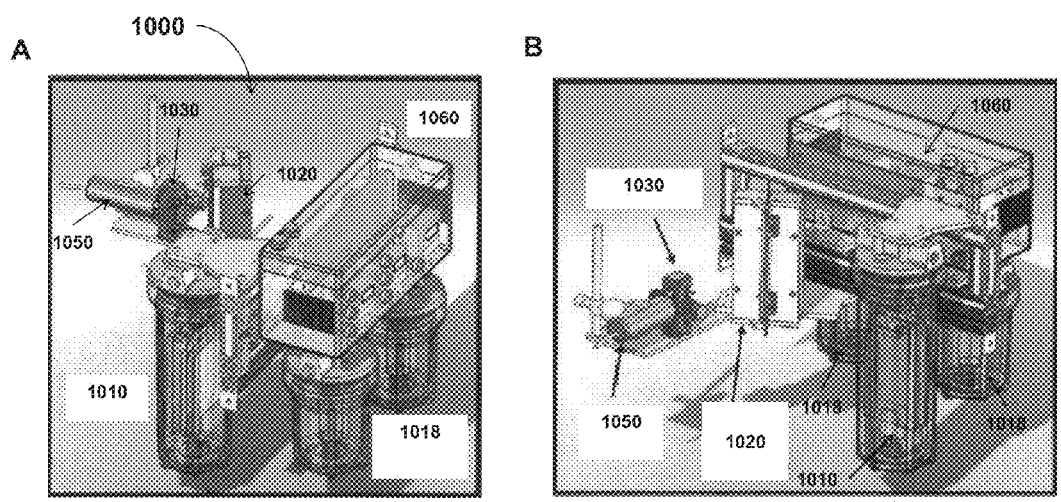
FIG. 10, Panels A-B are illustrations of the mechanical components of systems including a magnetic separation device and an acoustic concentrator, according to embodiments of the present disclosure.

Moreover, subject devices may in some aspects contain one or more additional components (see, e.g., FIG. 2 and FIG. 10, Panels A-B). Examples of such components include, but are not limited to, one or more valves (e.g., pinch valves, and the like), reservoirs (e.g., sample reservoirs, wash reservoirs, waste reservoirs, and the like), pumps (e.g., syringe pumps, peristaltic pumps, and the like), connective tubing (e.g., silicone tubing), housings, processors, and the like, as shall be described more fully herein. FIG. 2 illustrates an example of devices according to certain embodiments, where the device is in communication with a pump 201 to deliver sample 210 through pinch valve 202 into the inlet of magnetic separator 220. The outlet of magnetic separator 220 is in fluid communication with acoustic concentrator 230. Acoustic concentrator 230 may include a pinch valve 202a to collect sample which has passed through magnetic separator 220 but has not yet passed through the acoustic separator 230. Fluidic sample at the outlet of acoustic separator 230 may be passed though pinch valve 202c to waste compartment 218 which includes a source of waste air 203. Fluidic sample at the outlet of acoustic separator 230 is collected through pinch valve 202b which is in fluid communication with influx fluidics 240. Influx fluidics 240 includes a sorter flow cell 242, pinch valve 202d and sheath reservoir 244 having a supply of sheath air 245.

In some embodiments, subject devices include a conduit between the magnetic separation device and the acoustic concentrator device. The conduit positioned between the magnetic separation device and the acoustic concentrator device is in fluid communication with the outlet of the magnetic separation device and the inlet of the acoustic concentrator device. The conduit may be configured to direct a flow of the sample from the outlet of the magnetic separation device and into the inlet of the acoustic concentrator device. In certain aspects, the conduit is enclosed, such that the conduit is defined by outer walls that surround a central flow path. The central flow path may be aligned with a longitudinal axis of the conduit. The central flow path may have any convenient shape, such as, but not limited to, a flow path with a cross-sectional profile of a circle, an ellipse, a square, a rectangle, a pentagon, a hexagon, an irregular cross-sectional profile, combinations thereof, and the like.

During use, the conduit may also be configured to retain the sample received from the outlet of the magnetic separation device for a period time before delivering the sample to the acoustic concentrator device. For example, the conduit may be configured in certain instances to retain the sample received from the outlet of the magnetic separation device for 5 seconds or more, such as 5 seconds or more, such as 10 seconds or more, such as 30 seconds or more and including 60 seconds or more. For instance, the period of time may range from 5 seconds to 60 seconds, such as from 10 seconds to 50 seconds and including from 15 seconds to 45 seconds. The length of the conduit may vary, ranging from 1 cm to 30 cm, such as from 2 cm to 28 cm, such as from 5 cm to 25 cm and including from 10 cm to 20 cm.

In certain embodiments, the conduit may have a height (e.g., for conduits that do not have a round cross-sectional profile) or an inner diameter (e.g., for conduits that have a round cross-sectional profile) of 5 cm or less, such as 2 cm or less, including 1 cm or less, or 7 mm or less, or 5 mm or less, or 3 mm or less, or 2 mm or less, or 1 mm or less. The length of the conduit may range from 1 cm to 1000 cm, such as from 2 cm to 750 cm, including from 5 cm to 500 cm, or from 5 cm to 250 cm, or from 10 cm to 100 cm, such as from 10 cm to 50 cm, for example from 10 cm to 25 cm.

The conduit connecting the magnetic separation device and the acoustic concentrator may include one or more flow paths, as desired. Depending on the number of outlets from the magnetic separation device and the number of inlets to the acoustic concentrator device, the conduit may include 2 or more flow paths, such as 3 or more flow paths and including 5 or more flow paths. For example, the conduit positioned between the magnetic separation device and the acoustic concentrator device may include from 2 to 5 flow paths, such as 3 flow paths.

Various aspects of the embodiments of each of the magnetic separation device and the acoustic concentrator device shall now be described in greater detail below.

Magnetic Separation Device

Aspects of embodiments of the subject devices include one or more magnetic separation devices. A magnetic separation device may be configured to separate magnetically labeled moieties from non-magnetically labeled moieties (e.g., moieties that are not associated with a magnetic label) in a sample.

In certain instances, a magnetic separation device separates magnetically labeled moieties of interest from moieties that are not of interest (e.g., moieties that are not magnetically labeled) by retaining the magnetically labeled moieties in the device while not retaining moieties that are not of interest. Because the moieties of interest are magnetically labeled, the device may be configured to retain the magnetically labeled moieties in the device by attracting the magnetically labeled moieties to a magnetic field source in the device and retaining the magnetically labeled moieties in the device. In other cases, the device separates magnetically labeled moieties that are not of interest from moieties that are of interest (e.g., moieties of interest that are not magnetically labeled) by retaining the magnetically labeled moieties that are not of interest in the device while not retaining moieties that are of interest. In these embodiments, because the moieties of interest are not magnetically labeled, the moieties of interest are not retained in the device and flow through the device. The device may be configured to retain the magnetically labeled moieties that are not of interest in the device by attracting the magnetically labeled moieties to a magnetic field source in the device and retaining the magnetically labeled moieties that are not of interest in the device.

The magnetic separation device may be configured to separate magnetically labeled moieties from a simple sample or complex sample. By "simple sample" is meant a sample that includes one or more magnetically labeled moieties and few, if any, other molecular species apart from the solvent. By "complex sample" is meant a sample that includes the one or more magnetically labeled moieties of interest and also includes many other molecules that are not of interest, such as different proteins, cells, and the like. In certain embodiments, the complex sample is a blood sample, by which is meant blood or a fraction thereof, e.g., serum. In certain embodiments, the complex sample is a serum sample. In certain embodiments, the complex sample assayed using the devices disclosed herein is one that includes 10 or more, such as 20 or more, including 100 or more, e.g., $10^3$ or more, $10^4$ or more (such as 15,000; 20,000 or even 25,000 or more) distinct (i.e., different) molecular entities that differ from each other in terms of molecular structure.

Moieties of interest may include any moiety that can be stably associated with a magnetic label detectable by a magnetic separation device. By "stably associated" is meant that the magnetic label and the moiety of interest maintain their position relative to each other in space under the conditions of use, e.g., under the assay conditions. As such, the magnetic label and the moiety of interest can be non-covalently or covalently stably associated with each other. Examples of non-covalent associations include non-specific adsorption, binding based on electrostatic (e.g. ion, ion pair interactions), hydrophobic interactions, hydrogen bonding interactions, specific binding through a specific binding pair member covalently attached to the moiety of interest or the magnetic label, combinations thereof, and the like. Examples of covalent binding include covalent bonds formed between the magnetic label and a functional group present on the moiety of interest, e.g. —OH, where the functional group may be naturally occurring or present as a member of an introduced linking group. Accordingly, the magnetic label may be adsorbed, physisorbed, chemisorbed, or covalently attached to the surface of the moiety of interest.

Examples of magnetic separation devices of interest include, but are not limited to, those described in U.S. Pat. Nos. 5,945,281, 6,858,440; 6,645,777; 6,630,355; and 6,254,830; U.S. Patent Application No. PCT/US2012/032423; and Hoeppener, et al. (2012) *Recent Results Cancer Res.* 195:43-58; the disclosures of which are incorporated herein by reference.

Further embodiments and aspects of magnetic separation devices of interest are provided below.

Magnetic Field Source

Aspects of embodiments of magnetic separation devices include one or more magnetic field sources. The magnetic field source may be configured to produce a magnetic field. In certain cases, the magnetic field source produces an inhomogeneous magnetic field. By "inhomogeneous" is meant that the magnetic field has a magnetic field gradient, where the strength of the magnetic field is different depending on the position within the magnetic field. For instance, the magnetic field may have a magnetic field gradient, where the magnetic field strength is greater at one area and gradually decreases at positions further away from that area. Thus, the magnetic field source may be configured to produce a magnetic field having a magnetic field gradient.

In some instances, a magnetic separation device is configured to produce a magnetic field sufficient to separate the magnetically labeled moieties in the sample. The ability of the magnetic field to separate the magnetically labeled moieties in the sample may depend on various parameters, such as the magnetic field strength, the magnetic field gradient, the type of magnetic label, the size of the magnetic label, the distance between the magnetically labeled moieties and the magnetic field source, etc. In certain instances, the force the magnetic field is able to exert on a magnetic label is proportional to the magnetic field strength and the magnetic field gradient. In some cases, the magnetic field source is configured to produce a magnetic field having a magnetic force sufficient to separate magnetically labeled moieties form non-magnetically labeled moieties in the sample. For example, the magnetic field source may be configured to produce a magnetic field having a magnetic field gradient such that the product of the magnetic field and the magnetic field gradient is sufficient to separate magnetically labeled moieties from non-magnetically labeled moieties in the sample.

The magnetic field source may be of any shape that may facilitate the separation of the magnetically labeled moieties from the non-magnetically labeled moieties in the sample. For example, the magnetic field source may be elongated, such that the magnetic field source has a length that is greater than the transverse width of the magnetic field source.

In certain embodiments, a magnetic separation device may be configured to direct a flow of the sample through the magnetic separation device such that the sample flow is proximal to the magnetic field source. Minimizing the distance between the magnetic field source and the sample, and thereby minimizing the distance between the magnetic field source and the magnetically labeled moieties in the sample may facilitate the retention of the magnetically labeled moieties in the magnetic separation device. In some cases, a magnetic separation device is configured to direct the flow of the sample through the device to maximize the length of the flow path that is proximal to the magnetic field source. For example, the device may be configured to direct the flow of the sample through a magnetic separation device such that the sample flow is substantially parallel to the longitudinal axis of the magnetic field source.

In certain embodiments, a magnetic separation device includes one magnetic field source. In some cases, the magnetic field source is configured to produce a magnetic field sufficient to separate magnetically labeled moieties form non-magnetically labeled moieties in the sample. For example, the magnetic field source may be configured to produce a magnetic field sufficient to retain the magnetically labeled moieties in the device. In embodiments that include one magnetic field source, a magnetic separation device may be configured to direct the flow of the sample through the device such that the sample flows through an area near the magnetic field source. In some cases, a magnetic separation device is configured to direct the flow of the sample through the device such that the sample flow is substantially parallel to a longitudinal axis of the magnetic field source. A magnetic separation device may also be configured to direct the flow of the sample through an area near the magnetic field source, where the magnetic field and magnetic field gradient produced by the magnetic field source may be strongest.

In other embodiments, a magnetic separation device includes two magnetic field sources, although a magnetic separation device may include any number of magnetic field sources, such as 2, 3, 4, 5, 6, 7, 8, 9, 10, 15, 20, 25, 30, 35, 40, 45, or 50 or more magnetic field sources as desired. For instance, a magnetic separation device may include a first magnetic field source and a second magnetic field source. In some cases, the first magnetic field source and the second magnetic field source are configured to produce an inhomogeneous magnetic field (e.g., a magnetic field having a magnetic field gradient) sufficient to separate magnetically labeled moieties form non-magnetically labeled moieties in the sample. The first magnetic field source and the second magnetic field source may be configured to produce a magnetic field sufficient to retain the magnetically labeled moieties in the device. In certain embodiments, the first and second magnetic field sources are arranged such that a magnetic field is produced in an area between the magnetic field sources. As such, the first and second magnetic field sources may be configured to produce a magnetic field sufficient to retain the magnetically labeled moieties in an area between the magnetic field sources.

In certain embodiments, the first magnetic field source has a surface that faces the second magnetic field source, and the second magnetic field source has a surface that faces the first magnetic field source, such that these two surfaces are opposing each other. The surface of the first magnetic field source that faces the second magnetic field source may be substantially planar. Similarly, the surface of the second magnetic field source that faces the first magnetic field source may be substantially planar. In some instances, the surfaces of the first magnetic field source and the second magnetic field source that face each other are substantially parallel to each other. In these instances, the opposing surfaces of the first and second magnetic field sources may be a substantially uniform distance from each other. In other embodiments, the opposing surfaces of the first and second magnetic field sources are not parallel to each other, such that one end of the first magnetic field source is closer to the second magnetic field source than the opposite end of the first magnetic field source. In some cases, the first magnetic field source and the second magnetic field source are both elongated. The longitudinal axis of the first magnetic field source may be substantially parallel to the longitudinal axis of the second magnetic field source.

In embodiments that include a first magnetic field source and a second magnetic field source, the magnetization vectors of the first magnetic field source and the second magnetic field source may be aligned in substantially the same direction. In some instances, having a first magnetic field source and a second magnetic field source with magnetization vectors aligned in substantially the same direction facilitates the formation of a magnetic field and a magnetic field gradient in an area between the first and second magnetic field sources. In certain embodiments, the magnetization vector of the first magnetic field source is substantially perpendicular to the surface that faces the second magnetic field source. In some cases, the magnetization vector of the second magnetic field source is substantially perpendicular to the surface that faces the first magnetic field source. In certain instances, the magnetization vectors of the first and second magnetic field sources are both substantially perpendicular to the surfaces of the first and second magnetic field sources that face each other and are aligned in substantially the same direction.

In embodiments that include first and second magnetic field sources, the device may be configured to direct the flow of the sample through the device such that the sample flows through an area between the first magnetic field source and the second magnetic field source. In some cases, as described above, the first and the second magnetic field sources are aligned such that their longitudinal axes are substantially parallel. In these cases, the device may be configured to direct the flow of the sample through the device such that the sample flow is substantially parallel to the longitudinal axes of the first and second magnetic field sources. The device may also be configured to direct the flow of the sample through an area between the first and second magnetic field sources, where the magnetic field and magnetic field gradient produced by the first and second magnetic field sources may be strongest.

The magnetic field source may include a permanent magnet, an electromagnet, a superconducting magnet, combinations thereof, and the like. In certain embodiments, the magnetic field source includes one or more permanent magnets. A "permanent magnet" is a magnetic material that has a persistent magnetic field such that the magnetic field does not substantially decrease over time. In contrast, the term "soft magnet" refers to a material that can be magnetized in the presence of an applied external magnetic field, but whose magnetism substantially decreases when the external magnetic field is removed. In embodiments where the magnetic field source includes one or more permanent magnets, the use of permanent magnets may facilitate the production of a magnetic field without the need for external energy input into the device to power the magnetic field source. In some cases, a permanent magnet costs less than an electromagnet or a superconducting magnet that produces a magnetic field with a substantially similar magnetic field strength and magnetic field gradient. In these cases, the use of a permanent magnet may reduce the cost of the magnetic field source, and thus reduce the overall cost of the magnetic separation device. In certain cases, when the magnetic field source includes one or more permanent magnets, the use of a permanent magnet may facilitate the production of a magnetic separation device that is less complex than a magnetic separation device that includes an electromagnet and/or a superconducting magnet. For example, embodiments of the device that include a permanent magnet may not need to include components associated with an electromagnet and/or a superconducting magnet, such as a power source, electrical circuits associated with the magnetic field source, cooling components associated with the electromagnet and/or superconducting magnet, temperature sensors, and the like. In certain embodiments, the subject magnetic separation device does not include an electromagnet or superconducting magnet.

In some instances, the magnetic field source includes two or more permanent magnets. The permanent magnets may be of any desirable shape, and in some instances may be cube or bar-shaped permanent magnets. In certain embodiments, the permanent magnet is a cube or bar-shaped magnet having a substantially flat face positioned proximal to the conduit of the magnetic separation device. By having "a substantially flat face" is meant that the permanent magnet does not wrap (wholly or partially) around the conduit of the magnetic separation device. As such, in these embodiments, the magnet is a bar-shaped or cube-shaped permanent magnet having one of the flat edge faces of the magnet which is positioned adjacent to the conduit.

In certain cases, the magnetic field source may have a length ranging from 1 cm to 100 cm, such as from 1 cm to 75 cm, including from 1 cm to 50 cm, or from 1 cm to 25 cm, or from 1 cm to 10 cm, or from 5 cm to 10 cm, for example from 5 cm to 6 cm; a width ranging from 0.1 cm to 100 cm, such as from 0.1 cm to 75 cm, including from 0.1 cm to 50 cm, or from 0.1 cm to 25 cm, or form 0.1 cm to 10 cm, or from 0.1 cm to 5 cm, or from 0.1 cm to 2 cm, or from 0.5 cm to 2 cm, for example from 1 cm to 1.5 cm; and a height ranging from 0.1 cm to 100 cm, such as from 0.1 cm to 75 cm, including from 0.1 cm to 50 cm, or from 0.1 cm to 25 cm, or from 0.1 cm to 10 cm, or from 0.1 cm to 5 cm, or from 0.1 cm to 2 cm, or from 0.5 cm to 2 cm, for example from 1 cm to 1.5 cm. In certain embodiments, the length of the magnetic field source ranges from 3 cm to 5 cm.

The magnetic field source may be a permanent magnet, such as a rare-earth magnet. Rare-earth magnets include, but are not limited to, samarium-cobalt magnets (e.g., $SmCo_5$), neodymium alloy (NdFeB) magnets (e.g., $Nd_2Fe_{14}B$), and the like.

In certain embodiments, the magnetic field source produces a magnetic field ranging from 0.01 T to 10 T, or from 0.01 T to 5 T, or from 0.01 T to 2 T, or from 0.1 T to 2 T, or from 0.1 T to 1.5 T, including from 0.1 T to 1 T. In some cases, the magnetic field source is configured to produce a magnetic field with a magnetic field gradient (e.g., an absolute field gradient) ranging from 0.1 T/mm to 10 T/mm, such as from 0.1 T/mm to 7 T/mm, or from 0.1 T/mm to 5 T/mm, or from 0.1 T/mm to 3 T/mm, such as from 0.1 T/mm to 2 T/mm, including from 0.1 T/mm to 1 T/mm. In certain instances, the magnetic field source produces a magnetic field having a magnetic field gradient such that the product of the magnetic field and the magnetic field gradient (e.g., absolute field gradient) ranges from 0.001 $T^2$/mm to 100 $T^2$/mm, such as from 0.01 $T^2$/mm to 75 $T^2$/mm, including from 0.1 $T^2$/mm to 50 $T^2$/mm, or from 0.1 $T^2$/mm to 25 $T^2$/mm, or from 0.1 $T^2$/mm to 10 $T^2$/mm, or from 0.1 $T^2$/mm to 5 $T^2$/mm, or from 0.1 $T^2$/mm to 3 $T^2$/mm, such as from 0.1 $T^2$/mm to 2 $T^2$/mm, including from 0.1 $T^2$/mm to 1 $T^2$/mm.

In certain embodiments, the magnetic field source provides for a magnetic field gradient. The term magnetic field gradient is used in its conventional sense to refer to the density of magnetic field strength as a function of distance from the magnetic field source. In these embodiments, a magnetic field gradient is provided into the depth of the conduit of the magnetic separation device. In certain instances, no magnetic field gradient is produced along the length of the conduit of the magnetic separation device.

Magnetic Field Guides

Embodiments of magnetic separation devices include one or more magnetic field guides. The magnetic field guide may be configured to direct the magnetic field from the magnetic field source to the sample flow path. In certain instances, the magnetic field guide is configured to focus the magnetic field produced by the magnetic field source. The magnetic field guide may focus the magnetic field by increasing the magnetic flux of the magnetic field source, where the magnetic flux is the amount of magnetic field (e.g., the magnetic field density) that passes through a given surface area. The magnetic flux may depend on the magnetic field strength, the area of the surface and the angle between the magnetic field and the surface. For example, the magnetic field guide may focus the magnetic field, and thus increase the magnetic flux, by directing the magnetic field through a smaller area. In some cases, directing the magnetic field through a smaller area increases the magnetic field density, thus resulting in an increase in the magnetic flux. The magnetic field guides are configured to increase magnetic field density, in certain embodiments, by 5% or more as compared to the magnetic field density in the absence of the magnetic field guides, such as 10% or more, such as 25% or more, such as 50% or more, such as 75% or more, such as 90% or more and including 95% or more as compared to the magnetic field density in the absence of the magnetic field guides. For example, in these instances the magnetic field guides may be configured to increase the magnetic field density from 5% to 95%, such as from 10% to 90%, such as 15% to 85%, such as 20% to 80% and including from 25% to 75%. In other embodiments, the magnetic field guides are configured to increase magnetic field density by 2-fold or greater as compared to the magnetic field density in the absence of the magnetic field guides, such as 3-fold or greater, such as 4-fold or greater, such as 5-fold or greater and including 10-fold or greater as compared to the magnetic field density in the absence of the magnetic field guides. For example, in these instances the magnetic field guides may be configured to increase the magnetic field density from 2-fold to 10-fold, such as from 3-fold to 9-fold, such as from 4-fold to 8-fold and including from 5-fold to 7-fold.

The magnetic field source and the magnetic field guide may be configured to produce a magnetic flux sufficient to separate magnetically labeled moieties from non-magnetically labeled moieties in a sample. In some instances, the magnetic field guide is configured to produce a magnetic field having a magnetic flux density ranging from 0.01 T to 10 T, or from 0.01 T to 5 T, or from 0.01 T to 2 T, such as from 0.1 T to 2 T, including from 0.5 T to 1.5 T.

In certain cases, the magnetic field guide is configured to direct the magnetic field from the magnetic field source to the sample flow path with minimal loss in magnetic flux. In some cases, the magnetic field guide is configured to direct the magnetic field from the magnetic field source to the sample flow path with substantially no loss in magnetic flux. Without any intent to be bound by theory, the magnetic field guide may be configured to minimize the decrease in magnetic flux due to the self-demagnetization fields present in a soft magnet near the surfaces of the soft magnet. For example, the magnetic field guide may be configured to direct the magnetic field from the magnetic field source to the sample flow path with a decrease in magnetic flux of 50% or less from the initial magnetic flux, such as 40% or less, including 30% or less, or 25% or less, or 20% or less, or 15% or less, or 10% or less, or 7% or less, or 5% or less, for example 3% or less, or 2% or less, or 1% or less from the initial magnetic flux.

In certain embodiments, the magnetic field guide is configured to focus the magnetic field by having a portion with a tapered shape and by directing the magnetic field from the magnetic field source through the tapered portion of the magnetic field guide. By "tapered" is meant that a portion of the magnetic field guide has a wider end with a larger cross-sectional area and the cross-sectional area of the portion of the magnetic field guide becomes progressively smaller towards a narrower opposing end of the magnetic field guide. For example, the magnetic field guide may have a wedge-shaped portion, where the base of the wedge-shaped portion has an area. Cross-sections of the wedge-shaped portion taken parallel to the base of the wedge-shaped portion will have progressively smaller areas towards the end of the wedge-shaped portion opposite from the base (i.e., towards the apex edge of the wedge-shaped portion).

In some instances, the magnetic field guide has a wedge-shaped portion and is configured to direct the magnetic field from the base of the wedge-shaped portion to the apex edge of the wedge-shaped portion. Directing the magnetic field from the base of the wedge-shaped portion to the apex edge of the wedge-shaped portion may facilitate an increase in the magnetic flux of the magnetic field from the magnetic field source, as described above. An increase in the magnetic flux at the apex edge of the wedge-shaped portion of the magnetic field guide may produce a higher magnetic field and a higher magnetic field gradient proximal to the apex edge of the magnetic field guide than would be present in the absence of the magnetic field guide. Other tapered shapes for the magnetic field guide are possible, such as, but not limited to, pyramid, cone, frustum, combinations thereof, and the like.

In some instances, the magnetic field guide includes a portion that tapers to a point or an edge (e.g., the apex edge). For example, a cross-sectional profile of the magnetic field guide may taper to a point at the apex edge of the magnetic field guide. In other embodiments, the cross-sectional profile of the magnetic field guide tapers to a rounded edge such that the apex edge has a rounded (e.g., arcuate) cross-sectional profile at the apex edge. The term "wedge-shaped" as used herein is meant to include embodiments of the magnetic field guide that have an apex edge with a cross-sectional profile that tapers to a point at the apex edge. The term "wedge-shaped" also includes embodiments of the magnetic field guide that have an apex edge with a cross-sectional profile that does not taper to a point at the apex edge. For example, the apex edge of the magnetic field guide may have a cross-sectional profile that is rounded, truncated, blunted, and the like. The apex edge of the magnetic field guide may have a width that is approximately the same as the width (or diameter) of a conduit positioned adjacent the apex edge of the magnetic field guide. In certain embodiments, the apex edge of the magnetic field guide has a width that is less than the width (or diameter) of the conduit. In some cases, the width of the apex edge of the magnetic field guide is 5 mm or less, such as 4 mm or less, or 3 mm or less, or 2 mm or less, or 1 mm or less, or 0.5 mm or less, or 0.1 mm or less.

In certain instances, the apex edge of a wedge-shaped portion of the magnetic field guide has an apex angle, where the apex angle is the angle between the two faces of magnetic field guide that meet at the apex edge. In some cases, the apex angle is 150 degrees or less, or 135 degrees or less, such as 120 degrees or less, or 105 degrees or less, including 90 degrees or less, or 75 degrees or less, or 60 degrees or less, or 45 degrees or less, for example 30 degrees or less. In some embodiments, the apex angle is 60 degrees.

In certain embodiments, the apex edge of the magnetic field guide may be substantially parallel to a longitudinal axis of the magnetic field guide. In addition, the apex edge of the magnetic field guide may be substantially parallel to a longitudinal axis of the magnetic field source. In embodiments with one magnetic field source, the magnetic field source may have one or more magnetic field guides associated with the magnetic field source. For example, the magnetic field source may have a first magnetic field guide and a second magnetic field guide associated with the magnetic field source. In some embodiments, the device includes a first magnetic field guide disposed on a first surface of the magnetic field source, and a second magnetic field guide disposed on a second surface of the same magnetic field source. In some instances, the first and second magnetic field guides are disposed on opposite surfaces of the magnetic field source. In certain embodiments, the first magnetic field guide is wedge-shaped with a first apex edge, the second magnetic field guide is wedge-shaped with a second apex edge, and the first apex edge is aligned substantially across from and parallel to the second apex edge. The first apex edge may be positioned at a substantially uniform distance along its length from the second apex edge. In some cases, the magnetic field source includes a permanent magnet, as described above, and the first and second surfaces of the magnetic field source are the north and south poles of the magnetic field source.

In embodiments with more than one magnetic field source, each magnetic field source may have a magnetic field guide associated with it. Each magnetic field guide may be positioned such that the longitudinal axis of the magnetic field guide is substantially parallel to the longitudinal axis of the magnetic field source to which it is associated.

In certain embodiments, the apex edge of the magnetic field guide has a linear profile. By "linear" is meant that the apex edge of the magnetic field guide is substantially straight. In some instances, the apex edge of the magnetic field guide has a non-linear profile, such as, but not limited to, a saw-tooth, sinusoidal, square wave, triangular wave profile, combinations thereof, and the like. A magnetic field guide that has an apex edge with a non-linear profile may facilitate a local increase in the magnetic field and/or the magnetic field gradient near the non-linear portions of the apex edge.

The magnetic field guide may be proximal to the magnetic field source. In certain cases, the magnetic field guide is contacted with the magnetic field source. For example, the magnetic field guide may be attached to the magnetic field source to facilitate contact between the magnetic field guide and the magnetic field source. As described above, a magnetic separation device may include one magnetic field source. In these embodiments, the magnetic field source may include a wedge-shaped portion as described above. The magnetic field source may also include an extended portion between the wedge-shaped portion and the magnetic field source. The extended portion of the magnetic field guide may be configured to position the wedge-shaped portion at a distance away from the surface of the magnetic field source. For example, the extended portion of the magnetic field guide may contact the magnetic field source on a part of a first surface of the extended portion of the magnetic field guide. The extended portion of the magnetic field guide may extend a distance above the top surface of the magnetic field source. The part of the first surface of the extended portion of the magnetic field guide that extends above the top surface of the magnetic field source may have the wedge-shaped portion of the magnetic field guide. In some embodiments, the extended portion and the wedge-shaped portion of the magnetic field guide are contiguous (e.g., formed from the same piece of material). In other cases, the extended portion and the wedge-shaped portion of the magnetic field guide are separate pieces that are attached to each other. As described above, the device may also include a second magnetic field guide disposed on a surface of the magnetic field source opposite from the first magnetic field guide. Similar to the first magnetic field guide described above, the second magnetic field guide may include an extended portion and a wedge-shaped portion. The first and second magnetic field guides may be configured such that the apex edge of the wedge-shaped portion of the first magnetic field guide is proximal to the apex edge of the wedge-shaped portion of the second magnetic field guide. In some cases, the apex edge of the first magnetic field guide is substantially parallel to the apex edge of the second magnetic field guide. The apex edge of the first magnetic field guide may be aligned across from the apex edge of the second magnetic field guide. For example, the apex edge of the first magnetic field guide may be aligned substantially directly across from the apex edge of the second magnetic field guide. In certain embodiments, the apex edge of the first magnetic field guide is aligned substantially across from and substantially parallel to the apex edge of the second magnetic field guide. During use, the distance between the apex edge of the first magnetic field guide and the apex edge of the second magnetic field guide may be 5 cm or less, such as 2 cm or less, including 1 cm or less, or 7 mm or less, or 5 mm or less, or 3 mm or less, or 2 mm or less, or 1 mm or less.

In other embodiments as described above, a magnetic separation device may include two magnetic field sources, such as first and second magnetic field sources arranged proximal to each other. In some instances, a first magnetic field guide is associated with the first magnetic field source, and a second magnetic field guide is associated with the second magnetic field source. The first magnetic field guide may be positioned on the first magnetic field source on the surface of the first magnetic field source proximal to the second magnetic field source. For example, in embodiments where the magnetic field guides are wedge-shaped, the first magnetic field guide may be disposed on the first magnetic field source such that the base of the first magnetic field guide contacts the surface of the first magnetic source proximal to the second magnetic source. Similarly, the second magnetic field guide may be positioned on the second magnetic field source on the surface of the second magnetic field source proximal to the first magnetic field source. For example, in embodiments where the magnetic field guides are wedge-shaped, the second magnetic field guide may be disposed on the second magnetic field source such that the base of the second magnetic field guide contacts the surface of the second magnetic source proximal to the first magnetic source. In this arrangement, the first and second magnetic field guides may be positioned between the first and second magnetic field sources. In addition, the apex edge of the first magnetic field guide may be proximal to the apex edge of the second magnetic field guide. In some cases, the apex edge of the first magnetic field guide is substantially parallel to the apex edge of the second magnetic field guide. The apex edge of the first magnetic field guide may be aligned across from the apex edge of the second magnetic field guide. For example, the apex edge of the first magnetic field guide may be aligned substantially directly across from the apex edge of the second magnetic field guide. In certain embodiments, the apex edge of the first magnetic field guide is aligned substantially across from and substantially parallel to the apex edge of the second magnetic field guide. During use, the distance between the apex edge of the first magnetic field guide and the apex edge of the second magnetic field guide may be 5 cm or less, such as 2 cm or less, including 1 cm or less, or 7 mm or less, or 5 mm or less, or 3 mm or less, or 2 mm or less, or 1 mm or less.

Figure 3:
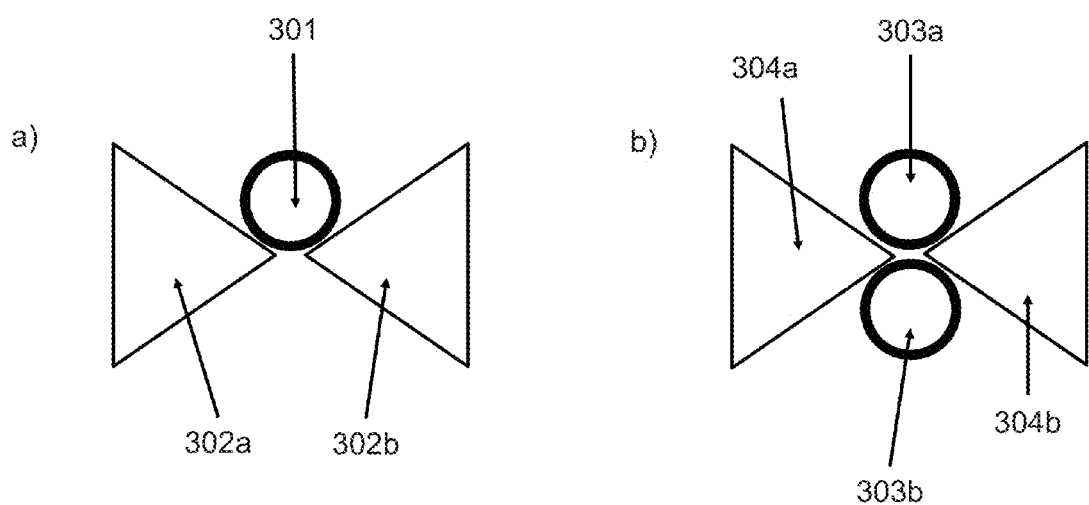
FIG. 3, Panel a is a diagram depicting a configuration of a flow channel positioned between a pair of wedge-shaped magnetic field guides in a magnetic separation device according to certain embodiments of the present disclosure.
Figure 3:
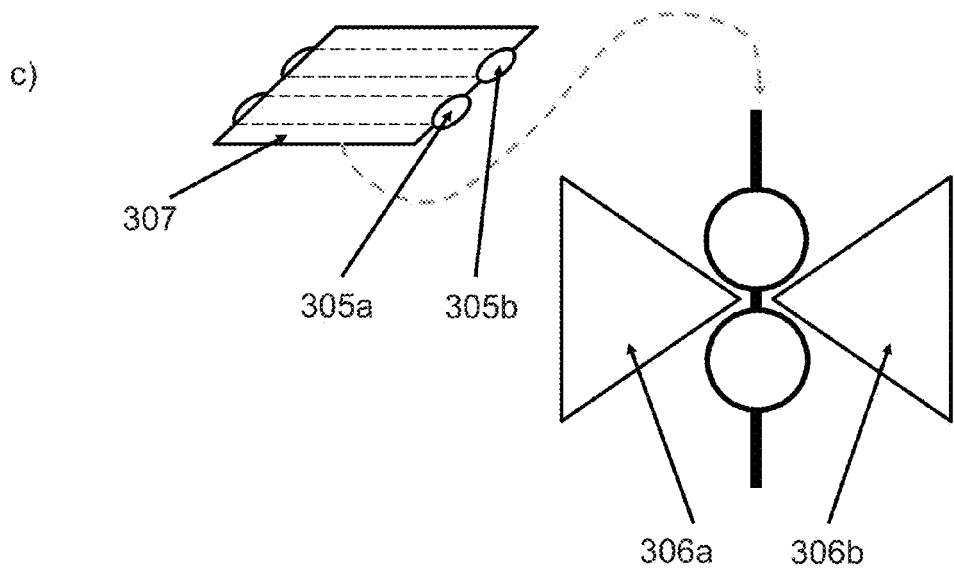

FIGS. 3a-c depict different types of flow channels positioned between a pair of wedge-shaped magnetic field guides. FIG. 3a depicts a configuration, where in certain embodiments, a single flow path 301 is positioned proximal to the apex of a pair of wedge-shaped magnetic field guides 302a and 302b. This configuration may be in certain instances repeated in parallel in the subject magnetic separation devices so as to create a plurality of parallel channels positioned between a pair of wedge-shaped magnetic field guides to increase flow capacity.

FIG. 3b depicts a configuration, where in certain embodiments, two flow channels 303a and 303b are positioned between a pair of wedge-shaped magnetic field guides 304a and 304b. In certain instances, this configuration may be repeated in parallel in the subject magnetic separation devices so as to create parallel channels positioned between a pair of wedge-shaped magnetic field guides to increase flow capacity.

FIG. 3c depicts another configuration of a pair of flow channels 305a and 305b positioned between a pair of wedge-shaped magnetic field guides 306a and 306b. As described in greater detail below, the flow channels may be formed by creating and inflating a hollow pathway through a pair of press sealed sheets 307 (e.g., rubber, plastic, etc.). In certain instances, this configuration may be in certain instances repeated in parallel in the subject magnetic separation devices so as to create a plurality of parallel channels positioned between a pair of wedge-shaped magnetic field guides to increase flow capacity.

Figure 4:
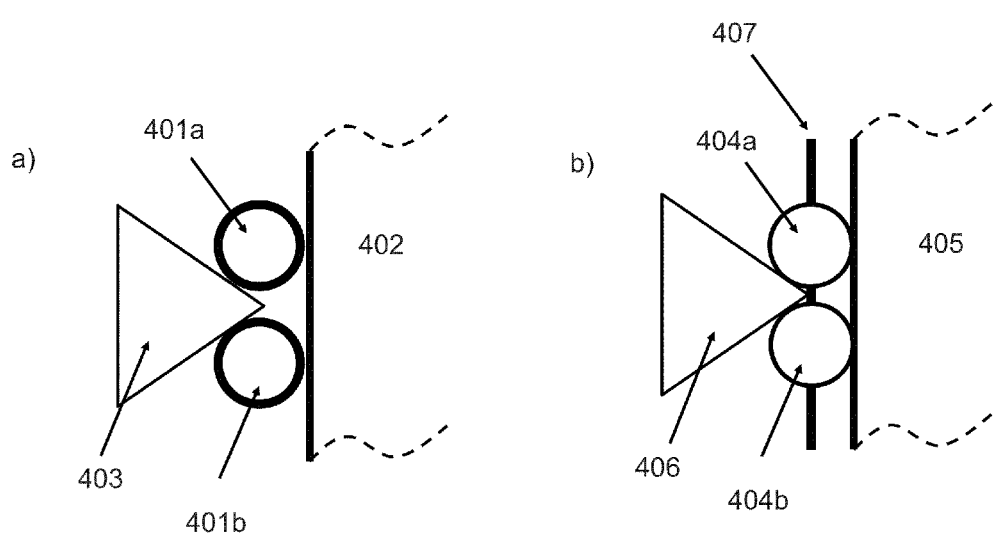
FIG. 4, Panel a is a diagram depicting a configuration of a plurality of flow channels positioned between to a wedge-shaped magnetic field guide and a flat-edge magnetic field guide in a magnetic separation device according to certain embodiments of the present disclosure.

FIGS. 4a-4b depict a configuration, according to certain embodiments, where a pair of flow channels are positioned between a wedge-shaped magnetic field guide and a flat-edge magnetic field guide. FIG. 4a depicts a configuration, where two flow paths 401a and 401b are positioned proximal to the apex of wedge-shaped magnetic field guide 403 and adjacent to flat-edge magnetic field guide 402. FIG. 4b depicts another configuration of two flow channels 404a and 404b positioned between a wedge-shaped magnetic field guide 406 and a flat-edge magnetic field guide 405. The flow channels (like the flow paths described in FIG. 3c above) may be formed by creating and inflating a hollow pathway through a pair of press sealed sheets 407 (e.g., rubber, plastic, etc.).

Figure 5:
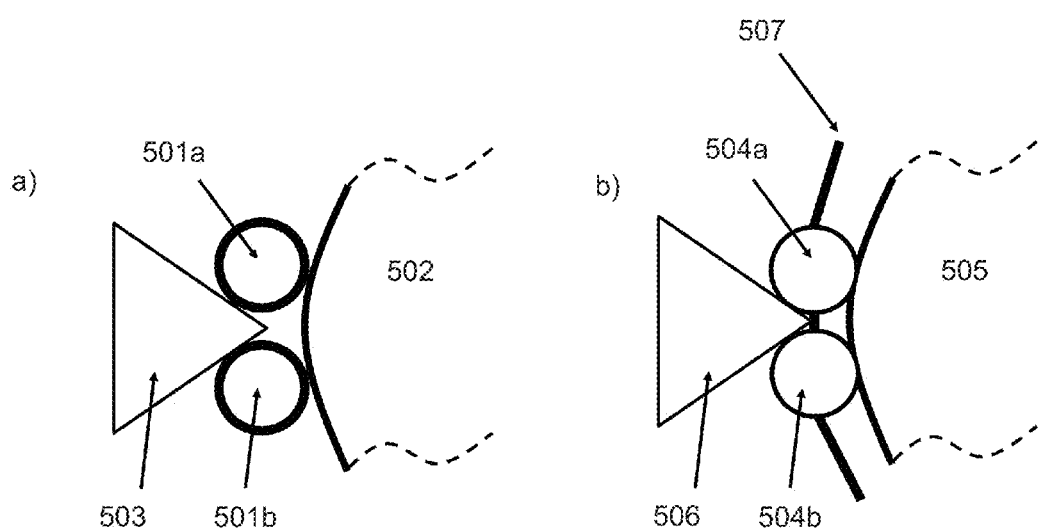
FIG. 5, Panel a is a diagram depicting a configuration of a plurality of flow channels positioned between a wedge-shaped magnetic field guide and a curved-edge magnetic field guide in a magnetic separation device according to certain embodiments of the present disclosure.

FIGS. 5a-5b depict a configuration, according to certain embodiments, where a pair of flow channels are positioned between a wedge-shaped magnetic field guide and a curved-edge magnetic field guide. FIG. 5a depicts a configuration, where two flow paths 501a and 501b are positioned proximal to the apex of wedge-shaped magnetic field guide 503 and adjacent to a curved-edge magnetic field guide 502. FIG. 5b depicts another configuration of two flow channels 504a and 504b positioned between a wedge-shaped magnetic field guide 506 and a curved-edge magnetic field guide 505. The flow channels (like the flow paths described in FIGS. 3c and 4b above) may be formed by creating and inflating a hollow pathway through a pair of press sealed sheets 507 (e.g., rubber, plastic, etc.).

As described above, the first and second magnetic field guides may be configured to focus the magnetic field produced by the magnetic field source. In certain instances, the first and second magnetic field guides focus the magnetic field to a region proximal to the apex edges of the first and second magnetic field guides. For example, the first and second magnetic field guides may focus the magnetic field in an area between the apex edges of the magnetic field guides. The first and second magnetic field guides may be configured to produce a magnetic flux proximal to the apex edges of the magnetic field guides sufficient to separate magnetically labeled moieties from non-magnetically labeled moieties in a sample. In some instances, the first and second magnetic field guides are configured to produce a magnetic field proximal to the apex edges of the magnetic field guides having a magnetic flux density ranging from 0.01 T to 10 T, or from 0.01 T to 5 T, or from 0.01 T to 2 T, such as from 0.1 T to 2 T, including from 0.5 T to 1.5 T.

Figure 6:
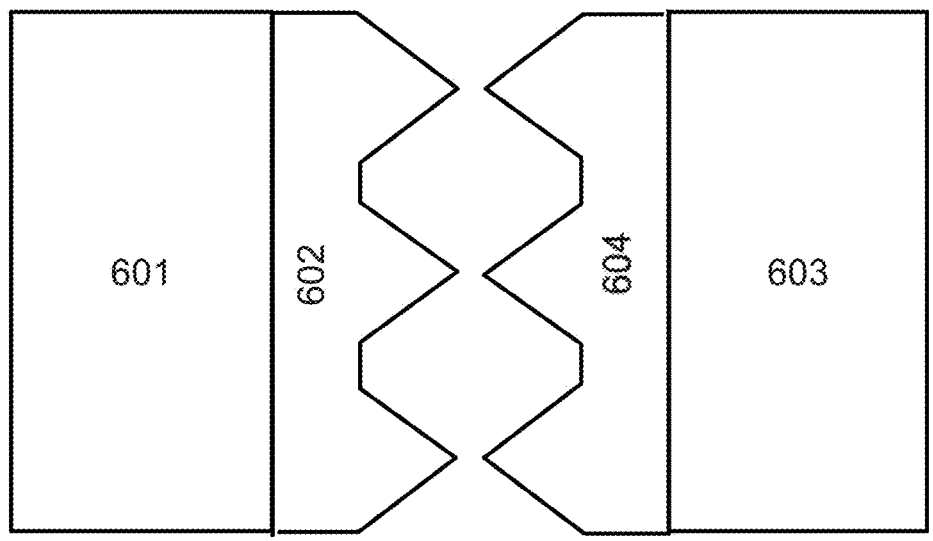
FIG. 6 depicts a configuration of a magnetic field source and magnetic field guide according to certain embodiments of the present disclosure.
Figure 7:
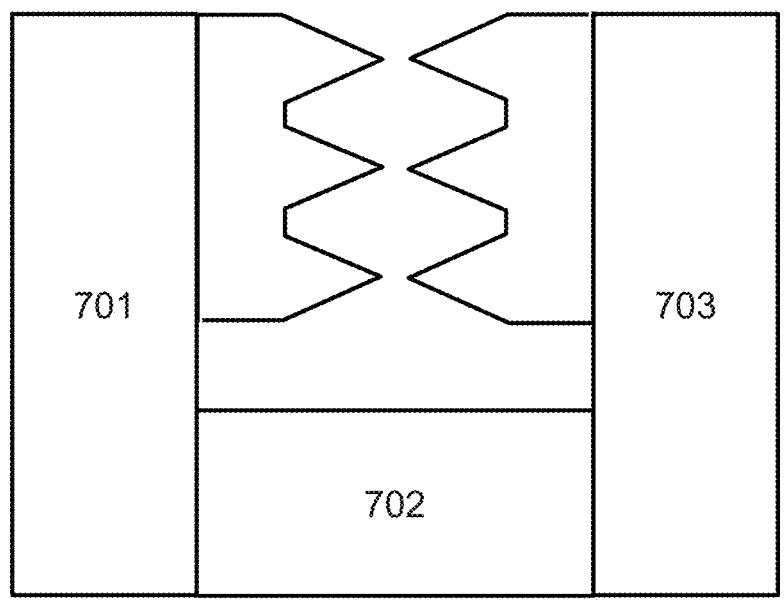
FIG. 7 depicts a configuration of a magnetic field source and magnetic field guides according to certain embodiments of the present disclosure.

In certain aspects, each magnetic field source is associated (e.g., attached) with a single magnetic field guide. FIG. 6 depicts two magnetic field sources (e.g., permanent magnets) 601 and 603 associated with magnetic field guides 602 and 604 having a multiple wedge (i.e., saw-tooth) configuration. The magnetic field guide may include any number of wedge shapes such as from 2 to 25, such as from 3 to 20, such as from 4 to 15, such as from 5 to 10 and including from 6 to 8. In certain embodiments, the magnetic field guide includes a 3-wedge configuration. In other embodiments, a magnetic field source may be associated (e.g. attached) with more than one magnetic field guide. FIG. 7 depicts a single permanent magnetic 702 coupled to two magnetic field guides 701 and 703 having a multiple wedge configuration.

In certain embodiments, the magnetic field guide includes a soft magnet. The term "soft magnet" refers to a material that can be magnetized in the presence of an applied external magnetic field, but whose magnetism substantially decreases when the external magnetic field is removed. Soft magnets may include, but are not limited to, ferromagnetic materials, such as iron (e.g., annealed iron), stainless steel and nickel, ferromagnetic materials, such as ceramic oxides of metals, combinations thereof, and the like.

In some instances, the magnetic field guide may have a length ranging from 1 cm to 100 cm, such as from 1 cm to 75 cm, including from 1 cm to 50 cm, or from 1 cm to 25 cm, or from 1 cm to 10 cm, or from 5 cm to 10 cm, for example from 5 cm to 6 cm; a width ranging from 0.1 cm to 100 cm, such as from 0.1 cm to 75 cm, including from 0.1 cm to 50 cm, or from 0.1 cm to 25 cm, or form 0.1 cm to 10 cm, or from 0.1 cm to 5 cm, or from 0.1 cm to 2 cm, or from 0.5 cm to 2 cm, for example from 1 cm to 1.5 cm; and a height ranging from 0.1 cm to 100 cm, such as from 0.1 cm to 75 cm, including from 0.1 cm to 50 cm, or from 0.1 cm to 25 cm, or from 0.1 cm to 10 cm, or from 0.1 cm to 5 cm, or from 0.1 cm to 2 cm, or from 0.5 cm to 2 cm, for example from 1 cm to 1.5 cm.

In certain embodiments, a magnetic separation device includes one or more magnetic flux sinks. The magnetic flux sink may be disposed on a surface of the magnetic field source. In some instances, the magnetic flux sink is disposed on a surface of the magnetic field source opposite the surface of the magnetic field source in contact with the magnetic field guide. In certain cases, the magnetic flux sink is configured to increase the magnetic field of the magnetic field source. The magnetic flux sink may be configured to increase the magnetic field of the magnetic field source by decreasing the self-demagnetization field of the magnetic field source (e.g., the self-demagnetization field of the permanent magnet). In some cases, the magnetic flux sink includes a soft magnet.

Conduit

Embodiments of a magnetic separation device may further include a conduit. The conduit may be configured to direct a flow of the sample through a magnetic separation device. As such, the conduit may be configured to carry the flow of the sample (e.g., a sample solution) in a channel, tube, well, etc. In certain embodiments, the conduit is enclosed, such that the conduit is defined by outer walls that surround a central flow path. The central flow path may be aligned with a longitudinal axis of the conduit. The central flow path may have any convenient shape, such as, but not limited to, a flow path with a cross-sectional profile of a circle, an ellipse, a square, a rectangle, a pentagon, a hexagon, an irregular cross-sectional profile, combinations thereof, and the like. During use, the conduit may also be configured to retain the magnetically labeled moieties in the sample.

In some instances, at least a portion of the conduit is positioned between the magnetic field guides, such as between the first magnetic field guide and the second magnetic field guide. The conduit may be positioned between the first and second magnetic field guides such that a longitudinal axis of the conduit is substantially parallel to a longitudinal axis of the first magnetic field guide and a longitudinal axis of the second magnetic field guide. For example, the conduit may be positioned between the apex edges of the first and second magnetic field guides such that the longitudinal axis of the conduit is substantially parallel to the apex edges of each of the first and second magnetic field guides. In some cases, positioning the conduit substantially parallel to the apex edges of the magnetic field guides maximizes the length of conduit, and thus the flow of sample fluid, that is between the apex edges of the magnetic field guides. In certain instances, positioning the conduit substantially parallel to the apex edges of the magnetic field guides maximizes the amount of time the flow of the sample is between the magnetic field guides. Aligning the conduit substantially parallel to the apex edges of the magnetic field guides may facilitate retaining the magnetically labeled moieties in the conduit.

In some instances, at least a portion of the conduit is positioned proximal to the magnetic field guides, such as adjacent the first magnetic field guide and the second magnetic field guide. In some instances, the conduit is positioned adjacent to, but not between, the apex edges of the first and second magnetic field guides. In certain cases, the conduit is positioned such that the conduit is in direct contact with an outer surface of one or more of the magnetic field guides. For example, the conduit may be positioned such that the conduit contacts the angled outer surface of the wedged-shaped portion of the magnetic field guides. In some cases, the conduit may not be positioned directly between the apex edges of the magnetic field guides, but rather adjacent to the apex edges and contacting an outer surface of the magnetic field guides as described above. The conduit may be positioned proximal to the first and second magnetic field guides such that a longitudinal axis of the conduit is substantially parallel to a longitudinal axis of the first magnetic field guide and a longitudinal axis of the second magnetic field guide. For example, the conduit may be positioned adjacent to the first and second magnetic field guides such that the longitudinal axis of the conduit is substantially parallel to the apex edges of each of the first and second magnetic field guides. In some cases, positioning the conduit substantially parallel to the apex edges of the magnetic field guides maximizes the length of conduit, and thus the flow of sample fluid, that is adjacent to the apex edges of the magnetic field guides. In certain instances, positioning the conduit substantially parallel to the apex edges of the magnetic field guides maximizes the amount of time the flow of the sample is proximal to the magnetic field guides. Aligning the conduit substantially parallel to the apex edges of the magnetic field guides may facilitate retaining the magnetically labeled moieties in the conduit.

In some instances, the conduit is configured to have a narrower cross-sectional area in the portion of the conduit positioned between the magnetic field guides. For example, the cross-sectional area of the conduit upstream from the portion of the conduit positioned between the magnetic field guides may be greater than the cross-sectional area of the portion of the conduit positioned between the magnetic field guides. Similarly, the cross-sectional area of the conduit downstream from the portion of the conduit positioned between the magnetic field guides may be greater than the cross-sectional area of the portion of the conduit positioned between the magnetic field guides. Thus, in some cases, a portion of the conduit positioned between the first and second magnetic field guides has a cross-sectional area less than the cross-sectional area of a portion of the conduit upstream or downstream from the portion of the conduit positioned between the first and second magnetic field guides.

In certain embodiments, the conduit may be positioned between the magnetic field guides manually. For example, the conduit may be manually aligned between the magnetic field guides, and may be manually removed from between the magnetic field guides. The conduit may be configured to have one or more alignment guides on the exterior of the conduit, such as, but not limited to, a notch, a tab, a groove, a guide post, etc., which may facilitate positioning of the conduit between the magnetic field guides. In some embodiments, the device may be configured to automatically position the conduit between the magnetic field guides. The conduit may include one or more markings or alignment guides as described above that the device may use to position the conduit between the magnetic field guides.

In some instances, the conduit is configured to be positionable away from the magnetic field, e.g., positionable away from the magnetic field sources and the magnetic field guides. Positioning the conduit away from the magnetic field may facilitate the recovery of magnetically labeled moieties that were retained in the conduit during an assay. In certain cases, the device may be configured to automatically position the conduit away from the magnetic field guides.

In certain cases, the conduit is configured to be reusable. A reusable conduit may be configured to be washed between assays, such as, but not limited to, configured to be washed by flowing a wash solution or buffer through the conduit between assays. In some cases, the conduit may be configured to be washed and reused without removing the conduit from the device. In other cases, the conduit may be configured to be removed from the device, washed and then reinserted into the device for a subsequent assay. In certain embodiments, the conduit is configured to be disposable. By disposable is meant that the conduit may be used once or several times (e.g., 20 times or less, 15 times or less, 10 times or less, or 5 times or less) and then discarded and replaced by a new conduit. For example, the conduit may be configured to be a single-use conduit, where the conduit is configured to be used for a single assay, and then removed and discarded. A new conduit may be used in a subsequent assay.

In certain embodiments, the conduit may have a height (e.g., for conduits that do not have a round cross-sectional profile) or an inner diameter (e.g., for conduits that have a round cross-sectional profile) of 5 cm or less, such as 2 cm or less, including 1 cm or less, or 7 mm or less, or 5 mm or less, or 3 mm or less, or 2 mm or less, or 1 mm or less. In certain embodiments, where the conduit has a round cross-sectional profile the inner diameter is 1 mm. The length of the conduit may range from 1 cm to 1000 cm, such as from 2 cm to 750 cm, including from 5 cm to 500 cm, or from 5 cm to 250 cm, or from 10 cm to 100 cm, such as from 10 cm to 50 cm, for example from 10 cm to 25 cm.

In certain embodiments, the conduit is configured to be substantially free from magnetic gradient enhancing materials. For example, the conduit may be made of non-magnetic and/or non-magnetizable materials. In some instances, the central flow path of the conduit is substantially free from magnetic gradient enhancing materials (excluding the magnetic labels themselves). For instance, the central flow path of the conduit may be substantially free of any materials (e.g., matrix materials, magnetizable particles (e.g., magnetizable spheres/ellipsoids), magnetizable wires, magnetizable cylinders, and the like) other than the sample (e.g., including any buffer and magnetic labels, etc. used in the assay itself). In some instances, having a conduit with a central flow path substantially free of materials, such as magnetizable materials, facilitates the subsequent recovery of the separated magnetically labeled moieties. For example, the separated magnetically labeled moieties may be more easily flushed from the conduit when the conduit is substantially free of materials as compared to a conduit with materials, such as magnetizable materials, in the central flow path of the conduit. The separated magnetically labeled moieties may be more easily flushed from the conduit, for instance, due to the absence of restrictions to the fluid flow path in a conduit substantially free of materials and/or the absence of magnetizable materials in the flow path that may have remnant magnetizations that retain the magnetically labeled moieties in the conduit.

In certain embodiments, the conduit includes a material that is flexible. When positioned between the magnetic field guides, the magnetic field guides, in some instances, may contact the surface of the conduit. In some cases, the first magnetic field guide (e.g., the apex edge of the first magnetic field guide) contacts a surface of the conduit, and the second magnetic field guide (e.g., the apex edge of the second magnetic field guide) contacts an opposing surface of the conduit. The magnetic field guides may be configured to contact the surfaces of the conduit without exerting significant pressure on the conduit. In other embodiments, a magnetic separation device is configured to compress the conduit between the apex edge of the first magnetic field guide and the apex edge of the second magnetic field guide. In some instances, the conduit is compressed such that the height (e.g., inner diameter) of the conduit is compressed to a fraction of the height of the conduit in the absence of any compression. For example, the conduit may be compressed to 90% or less of its initial height, such as 80% or less, including 70% or less, or 60% or less, or 50% or less of its initial height. In certain embodiments, the conduit is configured such that the conduit may be compressed near the center of the conduit, but may retain substantially the same height towards the outer edges of the conduit. In these embodiments, under compression, the conduit may have a central flow path with a height less than the height of the flow path near the outer edges of the conduit. Having a central flow path with a height less than the height of the flow path near the outer edges of the conduit may facilitate the retention of the magnetically labeled moieties in the conduit because the flow rate through the narrower center flow path of the conduit may be less than the flow rate through the wider periphery of the conduit.

In certain embodiments, the conduit includes one or more flow channels which are formed by creating and inflating one or more hollow pathways between a pair of sealed sheets. For example, the conduit may include two flow channels which are formed by inflating two parallel pathways between pressed sealed sheets of a polymeric material, such as, but not limited to, silicone, polypropylene, polyethylene, polyether ether ketone (PEEK), Teflon, and the like. In certain embodiments, the flow channels are formed by inflating a hollow pathway between sheets of a flexible material, such as a flexible polymer material (e.g., silicone, polyethylene, polypropylene, PEEK, etc.). Conduits, according to these embodiments, may include one more flow channels, such as 2 or more flow channels (e.g., see FIGS. 3c, 4b and 5b), such as 3 or more flow channels, such as 5 or more flow channels and including 10 or more flow channels, such as for example from 2 to 10 flow channels, such as from 3 to 9 flow channels, such as from 4 to 8 flow channels and including 5 flow channels. This configuration may in certain instances be repeated in parallel in the subject magnetic separation devices so as to create a plurality of parallel channels to increase flow capacity of the conduit.

In certain embodiments, the conduit includes a material that is rigid. When positioned between the magnetic field guides, the magnetic field guides, in some instances, may contact the surface of the conduit. In some cases, the first magnetic field guide (e.g., the apex edge of the first magnetic field guide) contacts a surface of the conduit, and the second magnetic field guide (e.g., the apex edge of the second magnetic field guide) contacts an opposing surface of the conduit. The magnetic field guides may be configured to contact the surfaces of the conduit without exerting significant pressure on the conduit.

The conduit may be made of any material that is compatible with the assay conditions, e.g., the sample solution buffer, pressure, temperature, etc. For example, the conduit may include materials that are substantially non-reactive to the sample, the moieties in the sample, the buffer, and the like. The conduit may include a flexible material, such that the conduit is flexible. In certain instances, the conduit is configured to deform from its initial shape and/or stretch if the conduit is compressed between the apex edges of the magnetic field guides, as described above. The conduit may be configured to deform from its initial shape and/or stretch without breaking, splitting, tearing, etc., when the conduit is compressed between the magnetic field guides. In some instances, the conduit includes glass, or polymers, such as, but not limited to, silicone, polypropylene, polyethylene, polyether ether ketone (PEEK), Teflon, and the like. In certain embodiments, the conduit includes a flexible material, such as a flexible polymer material (e.g., silicone, polyethylene, polypropylene, PEEK, etc.).

In some instances, the conduit has a cover layer disposed on the outer surface of the conduit. The cover layer may be configured to protect the conduit from the surrounding environment, and in some instances, may include one or more alignment guides to facilitate positioning the conduit between the magnetic field guides, as described above. The cover layer may include a flexible material, such that the cover layer is flexible and may deform from its initial shape and/or stretch. In certain instances, the cover layer is configured to deform from its initial shape and/or stretch if the conduit is compressed between the apex edges of the magnetic field guides as described above. The cover layer may be configured to deform from its initial shape and/or stretch without breaking, splitting, tearing, etc., when the conduit is compressed between the magnetic field guides. In certain embodiments, the conduit includes a flexible material, such as a flexible polymer material (e.g., silicone, polyethylene, polypropylene, PEEK, etc.).

Conduit Holder

In certain embodiments, a magnetic separation device includes a conduit holder operatively coupled to the conduit. In some cases, the conduit holder is configured to operatively couple the conduit to the magnetic separation device. For example, the conduit holder may be configured to facilitate positioning of the conduit between the magnetic field guides. In some cases, the conduit holder includes an elongated tab attached to the exterior of the conduit. The elongated tab may be attached to the exterior of the conduit such that the elongated tab is substantially parallel to a longitudinal axis of the conduit. In certain instances, the conduit holder facilitates positioning the conduit in the magnetic separation device such that a longitudinal axis of the conduit is substantially parallel to a longitudinal axis of the magnetic separation device, such as substantially parallel to the apex edges of the magnetic field guides as described above.

In some cases, the magnetic separation is configured to mate with the conduit holder operatively coupled to the conduit. For example, the magnetic separation device may be configured to have one or more mating elements, such as, but not limited to, a notch, a tab, a groove, a channel, a guide post, etc., which correspond to one or more corresponding alignment guides on the conduit holder. The one or more mating elements may facilitate positioning the conduit between the magnetic field guides of the magnetic separation device. In some cases, the magnetic separation device includes a channel configured to mate with the conduit holder. The channel may be configured to position the conduit holder in the magnetic separation device such that the longitudinal axis of the conduit is substantially parallel to a longitudinal axis of the magnetic separation device, such as substantially parallel to the apex edges of the magnetic field guides as described above.

In certain embodiments, the conduit holder may be positioned between the magnetic field guides manually. For example, the conduit holder may be manually positioned in the magnetic separation device by aligning the conduit holder with the corresponding mating element (e.g., channel) of the magnetic separation device. In some cases, the conduit holder may be manually removed from the magnetic separation device. In some embodiments, the device may be configured to automatically position the conduit holder in the magnetic separation device. The conduit holder may include one or more markings or alignment guides as described above that the device may use to automatically position the conduit holder in the magnetic separation device.

Acoustic Concentrator Device

As described above, aspects of embodiments of devices of the present disclosure may include one or more acoustic concentrator devices. In the subject devices, one or more acoustic concentrators may be upstream, downstream, or both from one or more magnetic separation devices.

As used herein, the terms "acoustic concentrator device" and "acoustic separator device" are used broadly and generically to refer to a device in which particulate matter in a fluid may be controlled or manipulated by means of ultrasonic standing waves, and the terms may be used interchangeably. Accordingly, in certain aspects, an acoustic concentrator device may be used to sort components in a fluid sample. In certain aspects, an acoustic concentrator device may instead, or also, be used to concentrate components in a fluid sample. Acoustic concentrator devices of interest include, but are not limited to, those described in U.S. Pat. No. 6,929,750; Laurell, et al. (2007) Chem. Soc. Rev., 2007, 36, 492-506; Petersson, et al. (2005) Analytical Chemistry 77: 1216-1221; and Augustsson, et al. (2009) Lab on a Chip 9: 810-818; the disclosures of which are incorporated herein by reference.

Figure 8:
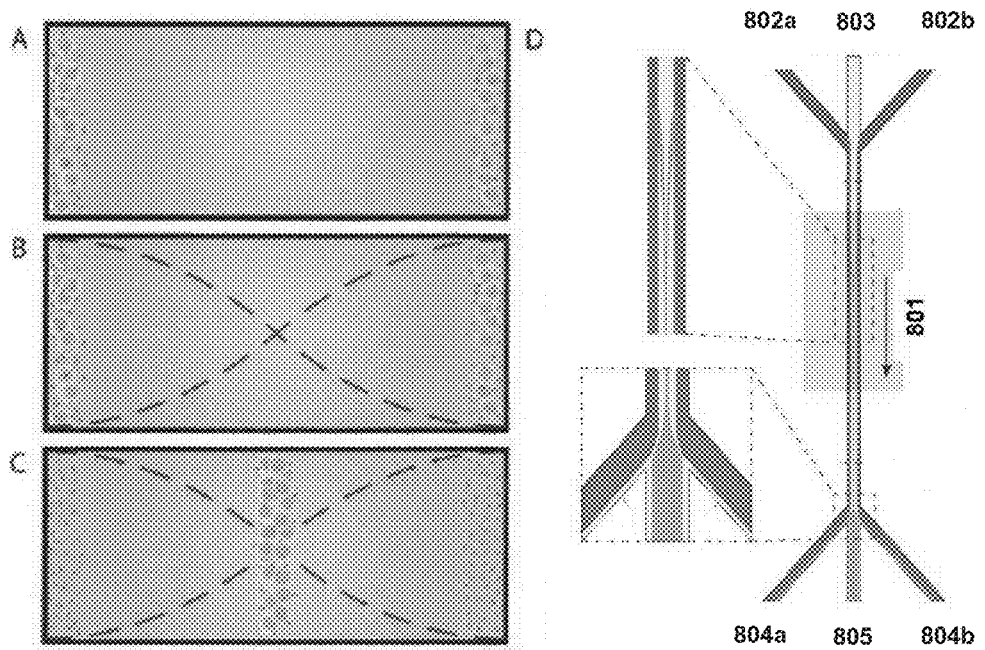
FIG. 8, Panels A-D are illustrations of an acoustic concentrator device. Panels A-C: Side views of an acoustic concentrator device flow channel. Particles begin by flowing along the sides of the channel (Panel A). An acoustic standing wave may be induced in the channel (e.g., using a vibration generator, such as a piezoelectric transducer, placed adjacent to the channel), as indicated by the dashed lines (Panels B-C). The acoustic standing wave creates a pressure node in the center of the channel (Panel B). Particles present in the channel may move towards the pressure node (Panel C). Panel D: Top view of an acoustic concentrator device flow channel. In this example, the direction of fluid flow is from the top to the bottom of the figure. The acoustic concentrator includes two sample inlets and a buffer inlet. With the inputs arranged as illustrated, the sample fluid (dark gray) flows along the sides of the channel, with the buffer (light gray) flowing between. A piezoelectric transducer is located below the channel which, when activated, creates an acoustic standing wave in the channel. The acoustic standing wave causes certain particles contained in the samples to move from the sides of the channel towards the pressure node formed in the center of the channel (as indicated by the focusing zone; top inset). These particles, now contained in buffer, are collected by the washed sample outlet. Two outlets placed at the sides of the channel collect waste.

General principles of certain aspects of acoustic concentrator devices are illustrated in FIG. 8, Panels A-D. FIG. 8, Panel D is a schematic depiction of a microfluidic acoustic concentrator device that allows for the concentration and/or sorting of cells in a sample by acoustic concentration. In this example, the direction of fluid flow 801 is from the top to the bottom of the figure. The acoustic concentrator device includes two sample inlets 802a and 802b and a buffer inlet 803. With the inputs arranged as illustrated, the sample fluid (purple) flows along the sides of the channel, with the buffer (yellow) flowing between, with the fluids operating under laminar flow. As such, the first liquid medium and the second liquid medium are combined in a manner sufficient to produce a laminar flow of the first and second media, i.e., a flow in which the two media are flowing in distinct but adjacent and contacting flow paths. The densities of the first and second media differ in some instances in order to facilitate the manipulation of a component from a first media to a second media, or vice versa, where in some instances the density difference between the first and second media is 1% or greater, such as 5% or greater, including 10% or greater. A piezoelectric transducer is located below the channel which, when activated, creates an acoustic standing wave in the channel. The acoustic standing wave causes certain particles contained in the samples to move from the sides of the channel in the first media towards the pressure node formed in the center of the channel (as indicated by the focusing zone; top inset) in the second media. As shown in FIG. 8, the particles (e.g., cells), now contained in buffer are collected by the washed sample outlet 805. Two outlets 804a and 804b placed at the sides of the channel collect waste.

In some embodiments, the acoustic standing wave is focused to the center of the flow channel. In these embodiments, the acoustic standing wave is configured to propagate within the channel applying a radial acoustic radiation pressure within the flow channel. In certain instances, the applied acoustic standing wave does not propagate outside of the flow channel. In certain embodiments, the acoustic field is applied only in a single direction by the vibration transducer. As such, in these embodiments the vibration transducer does not simultaneously apply acoustic fields in two or more different directions.

In certain aspects, an acoustic concentrator device does not include a plurality of inputs. For example, the microfluidic acoustic concentrator device depicted in FIG. 8, Panel D may instead be operated in a manner where a sample fluid is input through the center inlet, with the outer inlets not present, not used, and/or blocked off. In such embodiments, a sample containing particles may flow through the center inlet, pass over the piezoelectric transducer, and be collected by the washed sample output. The acoustic standing wave causes certain particles contained in the sample to become concentrated, such that these particles (e.g., cells) are present in the sample collected by the washed sample outlet at a higher concentration relative to the concentration of the particles in the sample fluid input to the acoustic concentrator device.

General principles of certain aspects of acoustic concentrator devices are illustrated in FIG. 8, Panels A-C, which provide cross-section illustrations of an acoustic concentrator device channel. As depicted in these panels, particles begin by flowing along the sides of the channel (FIG. 8, Panel A). An acoustic standing wave may be induced in the channel (e.g., using a vibration generator, such as a piezoelectric transducer, placed adjacent to the channel), as indicated by the dashed lines (FIG. 8, Panels B-C). The acoustic standing wave creates a pressure node in the center of the channel (FIG. 8, Panel B). Certain particles present in the channel may move towards the pressure node (FIG. 8, Panel C), depending upon their physical properties. Generally, molecules and particles smaller than about 1 micron in diameter are not affected by the acoustic standing wave(s).

The mechanism by which acoustic concentrator devices operate is described in, for example, Laurell, et al. (2007) Chem. Soc. Rev., 2007, 36, 492-506. Briefly, an acoustic contrast factor (also called an $\phi$-factor) depends on both a particle's (e.g., a cell) density ($\rho_c$) and its compressibility ($\beta_c$) in relation to the corresponding properties of the surrounding medium ($\rho_w$, $\beta_w$). An acoustic contrast factor may be positive or negative, which determines the direction of the acoustic force and whether a particular particle will move towards a standing pressure wave node (i.e., the center of the image in FIG. 8, Panel B) or towards the pressure antinode (i.e., the sides of the channel in FIG. 8, Panel B). Generally, solid particles in aqueous media are moved towards a pressure node. Accordingly, depending on the application, the shape and dimensions of the channel(s), the materials from which the acoustic concentrator device channel is made, the number of inlets and outlets employed, the flow rate in the channel, the frequency of ultrasound applied, and other parameters of an acoustic concentrator device may vary.

In certain aspects, an acoustic concentrator device may be based upon the Lund-method, in which acoustic concentration or separation of suspended particles is based on a laminar flow microchannel that is ultrasonically actuated from below using a vibration generator, such as a piezoelectric ceramic. The width of the channel may be chosen to correspond to half the desired ultrasonic wavelength, thereby creating a resonator between the side walls of the flow channel in which a standing wave can be formed. The induced standing wave may thus be generated orthogonal to the incident ultrasonic wave front. As suspended particles with a positive $\phi$-factor perfuse the channel they are moved, by means of the axial primary radiation force (PRF), towards the pressure nodal plane along the channel center, while those with a negative $\phi$-factor are moved towards the anti-nodal planes close to the side walls (FIG. 8, Panel C). The end of the separation channel is split into three or more outlet channels, thus allowing the positive $\phi$-factor particles to exit through a center outlet and the negative $\phi$-factor particles to exit through side outlets (FIG. 8, Panel D).

The channel may have any convenient configuration. While the cross sectional shape may vary, in some instances, cross-sectional shapes of channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc.

Acoustic concentrator devices may be manufactured from any convenient rigid material. In certain aspects, one or more flow channels are made by etching (e.g., anisotropically etching) a channel in silicon, steel, glass (e.g., Pyrex glass), Poly(methyl methacrylate), polycarbonate, or any other convenient material. The channel(s) may be sealed using a membrane sealed atop the channel. Any convenient membrane type may be used, such as glass (e.g., boron silica glass). In certain embodiments, the flow channel consists of pyrex glass. In other embodiments, the flow channel consists of boron silica glass. In some embodiments, the flow channel does not include any reflective surfaces within or along the surface which may be configured for reflecting or altering the propagation of the acoustic wave. In other embodiments, the flow channel does not include any capture agents or surface etching for trapping particles along the surface of the flow channel.

In certain aspects, a vibration generator is bonded to the bottom of the channel. Vibration generators of interest include, but are not limited to, piezoelectric transducers such as PZT. In certain aspects, the piezoelectric transducer is of the multi-layer type, but a bimorph piezoelectric element may also be used as well as any other kind of ultrasound generating element with suitable dimensions. In some embodiments, the vibration transducer and the flow channel may be integrated together in the acoustic concentrator device. In these embodiments, the vibration transducer and the flow channel form a single component acoustic concentrator device.

The vibration generator may be of any desirable shape, and in some instances may be a cube or bar-shaped piezoelectric transducer. In certain embodiments, the vibration generator is a cube or bar-shaped piezoelectric transducer having a substantially flat face positioned proximal to the conduit of the acoustic concentrator device. By "having a substantially flat face" is meant that the vibration generator does not wrap (wholly or partially) around the conduit of the acoustic concentrator device. As such, in these embodiments, the vibration generator is bar-shaped or cube-shaped having one of the flat edge faces positioned proximal to the conduit. In certain embodiments, the frequency of the acoustic wave that is applied corresponds to the fundamental resonance mode of the vibration transducer (e.g., about 2 MHz for many PZT plates). The frequency may, in some embodiments, instead correspond to a harmonic of the vibration transducer, such as a first harmonic, second harmonic, and the like. In various aspects, the frequency applied may be about 1.5 MHz or more, including about 1.9 MHz or more, such as about 2.0 MHz to about 2.1 MHz, about 2.1 to about 2.2 MHz, about 2.2 MHz to about 2.3 MHz, about 2.3 to about 2.4 MHz, about 2.5 MHz to about 3.0 MHz, about 3.0 MHz to about 3.5 MHz, about 3.5 to about 4.0 MHz, about 4.0 MHz to about 5.0 MHz, or about 5.0 MHz or higher.

In certain embodiments, the amplitude of acoustic wave remains constant when applied to the sample flow in the acoustic concentrator device. As such, in these embodiments, the amplitude of the applied acoustic wave is configured to increase or decrease by 2% or less when applied to the sample flow in the acoustic concentrator device, such as by 1.5% or less, such as by 1% or less, such as by 0.5% or less, such as by 0.25% or less, such as by 0.1% or less, such as by 0.05% or less and including 0.01% or less. The amplitude of the acoustic wave applied may vary depending on the density and rate of particles and fluid flowing through the acoustic concentrator device and may be about 5 dB referenced to 20 micro-Pascals or more, such as 25 dB referenced to 20 micro-Pascals or more, such as 50 dB referenced to 20 micro-Pascals or more, such as 100 dB referenced to 20 micro-Pascals or more and including 200 dB referenced to 20 micro-Pascals or more, such as from about 5 to about 25 dB referenced to 20 micro-Pascals, such as from about 25 to about 50 dB referenced to 20 micro-Pascals or more, such as from about 50 to about 75 dB referenced to 20 micro-Pascals, such as from about 75 to about 100 dB referenced to 20 micro-Pascals, such as from about 100 to about 125 dB referenced to 20 micro-Pascals, such as from about 125 to about 150 dB referenced to 20 micro-Pascals, such as from 150 to about 175 dB referenced to 20 micro-Pascals and including from about 175 to about 200 dB referenced to 20 micro-Pascals.

The activation voltage that is applied may also vary. For example, in certain aspects an activation voltage is about 0.1 $V_{pp}$ to about 100 $V_{pp}$ or higher, such as about 0.1 $V_{pp}$ to about 1 about 1 $V_{pp}$ to about 10 about 10 $V_{pp}$ to about 20 $V_{pp}$, about 20 $V_{pp}$ to about 30 $V_{pp}$, about 30 $V_{pp}$ to about 40 $V_{pp}$, about 40 $V_{pp}$ to about 50 $V_{pp}$, about 50 $V_{pp}$ to about 75 $V_{pp}$, about 75 $V_{pp}$ to about 100 $V_{pp}$, or about 100 $V_{pp}$ or higher.

In certain aspects, the dimensions for a channel in which to perform acoustic concentration are about 375 μm×about 150 μm×about 30-70 mm. In other aspects, the channel may vary, for example from about 100-550 μm×about 50-250 μm×about 20-100 mm.

In certain aspects, an acoustic concentrator device may be controlled by a processor configured to control the vibration generator. The processor may be contained within a control unit or control box (see, e.g., FIG. 10, Panels A-B). In certain aspects, the processor is configured to control the vibration generator by altering one or more of the shape, frequency and power of the electrical energy delivered to the vibration generator. As illustrated in FIG. 10, device 1000 includes sample reservoir 1010, wash and waste reservoirs 1018, magnetic assembly 1020, control box 1060, camera 1050 and chip assembly 1030.

The flow rate of an acoustic concentrator device may vary. In certain embodiments, the flow rate of the acoustic concentrator device is adjusted such that the output from the acoustic concentrator device is optimal for subsequent analysis, such as about 20 to 150 μL/min, including about 30 to 100 μL/min, such as about 40-60 μL/min. The flow rate of the acoustic concentrator device may be adjusted such that the output from the acoustic concentrator device is optimal for subsequent analysis by a particular device, such as a BD Biosciences Influx™ cell sorter. In certain aspects, the acoustic concentrator device is used to reduce the flow rate from a magnetic separator, such that the output from the acoustic concentrator device is optimal for subsequent analysis and/or tailored for a particular device, such as a BD Biosciences Influx™ cell sorter.

In certain aspects, the flow rate of an acoustic concentrator device may be controlled by modulating one or more pumps (e.g., a syringe pump, such as a WPI sp210iwz distributed by World Precision Instruments Inc., Sarasota, Fla.) or valves (e.g., pinch valves). The flow rate may, in certain embodiments, be controlled by a processor, such as a processor described above.

In certain aspects, the rate at which one or more acoustic concentrator devices sort and/or concentrate cells is about 1 μl/min or more. For example, in certain aspects the rate is about 10 μl/min or more, including about 10 μl/min to about 50 μl/min, about 50 μl/min to about 100 μl/min, about 100 μl/min to about 200 μl/min, about 200 μl/min to about 300 μl/min, about 300 μl/min to about 400 μl/min, about 400 μl/min to about 500 μl/min, about 500 μl/min to about 600 μl/min, about 600 μl/min to about 700 μl/min, about 700 μl/min to about 800 μl/min, about 800 μl/min to about 900 μl/min, about 900 μl/min to about 1 ml/min, about 1 ml/min to about 10 ml/min, about 10 ml/min to about 20 ml/min, about 20 ml/min to about 30 ml/min, about 30 ml/min to about 40 ml/min, about 40 ml/min to about 50 ml/min, about 50 ml/min to about 60 ml/min, about 60 ml/min to about 70 ml/min, about 70 ml/min to about 80 ml/min, about 80 ml/min to about 90 ml/min, about 90 ml/min to about 100 ml/min, about 100 ml/min to about 150 ml/min, about 150 ml/min to about 200 ml/min, about 200 ml/min to about 500 ml/min, or about 500 ml/min to 1 L/min. In certain aspects, the flow rate of the acoustic concentrator device is adjusted such that the output from the acoustic concentrator device is optimal for subsequent analysis, such as about 20 to 150 μL/min, including about 30 to 100 μL/min, such as about 40-60 μL/min. The flow rate of the acoustic concentrator device may be adjusted such that the output from the acoustic concentrator device is optimal for subsequent analysis by a particular device, such as a BD Biosciences Influx™ cell sorter.

In some embodiments, fluidic flow through the acoustic concentrator device is laminar. The term "laminar flow" is used in its conventional sense to refer to the flow dynamic where fluid flows in a plurality of parallel layers which little to no disruption between the layers. For instance, a stream of sheath buffer may be laminated between two streams of sample in the flow through the acoustic concentrator device. In these embodiments, when an acoustic field is applied, whole cells (e.g., lymphocytes) or particles of higher density are forced radially to a node of the acoustic standing wave in a laminate of flowing wash buffer. The concentrated sample may exit the acoustic concentrator device through a dedicated sample outlet while particles in parallel laminating sample streams may be directed to distinct, separate outlets.

In certain aspects, the subject acoustic concentrator device is configured to apply acoustic radiation pressure which is sufficient to separate particles in the flow stream based on predetermined particle size. By varying the frequency of the applied acoustic wave and amplitude of radial acoustic pressure the acoustic concentrator device is configured, in these embodiments, to selectively concentrate particles of a predetermined size. For example, in some instances, the acoustic concentrator device is configured to apply acoustic radiation pressure which is sufficient to concentrate particles which have diameters of 10 μm or greater, such as 25 μm or greater, such as 50 μm or greater and including 100 μm or greater, such as from 10 to 25 μm, such as from 25 to 50 μm, such as from 50 to 75 μm and including from 75 to 100 μm. For instance, by varying acoustic wave frequency and amplitude the acoustic concentrator may be configured to separate whole cells (e.g., lymphocytes) from cellular debris, protein, among other lysate impurities, as desired.

In certain aspects, to achieve a desired flow rate a plurality of parallel separation channels may be used in one or more acoustic concentrator devices. For example, in certain aspects two or more parallel separation channels are used, including 3 or more, such as 5 or more, 8 or more, 15 or more, 25 or more, 40 or more, 60 or more, 80 or more, 100 or more, 125 or more, 150 or more, 200 or more, 300 or more, 400 or more, 500 or more, or 1000 or more. The separation channels may be contained on one or more chips, such as 2 or more, 5 or more, 10 or more, 20 or more, 50 or more, or 100 or more. Moreover, a plurality of vibration transducers may be used, such as 2 or more, 5 or more, or 10 or more. In certain embodiments, the acoustic concentrator device includes a single transducer, such as a single piezoelectric transducer.

In certain aspects, two or more separation channels are arranged in series. Any convenient number of acoustic concentrator devices and/or separation channels may be arranged in series and/or in parallel to facilitate sorting and/or concentrating components in a fluid sample.

Accordingly, in some embodiments, the subject methods may involve the use of two or more acoustic concentrator devices, such as 3 or more, including 4 or more, 5 or more, 6 or more, or 7 or more. Such acoustic concentrator devices may be arranged in any convenient configuration, such as in a serial configuration, parallel configuration, or a combination of the two. Moreover, the acoustic concentrator devices may be substantially identical, identical, or heterogeneous (e.g., differ in one or more ways, such as in the dimensions of the flow channel, the applied voltage, the oscillation frequency, etc.).

Moreover, the acoustic concentrator devices used in practicing the subject methods may in some aspects contain one or more additional components. Examples of such components include, but are not limited to, one or more valves (e.g., pinch valves, and the like), reservoirs (e.g., sample reservoirs, wash reservoirs, waste reservoirs, and the like), pumps (e.g., syringe pumps, peristaltic pumps, and the like), connective tubing (e.g., silicone tubing), housings, processors, and the like.

Systems

Also provided are systems that include one or more devices of the present disclosure.

Figure 9:
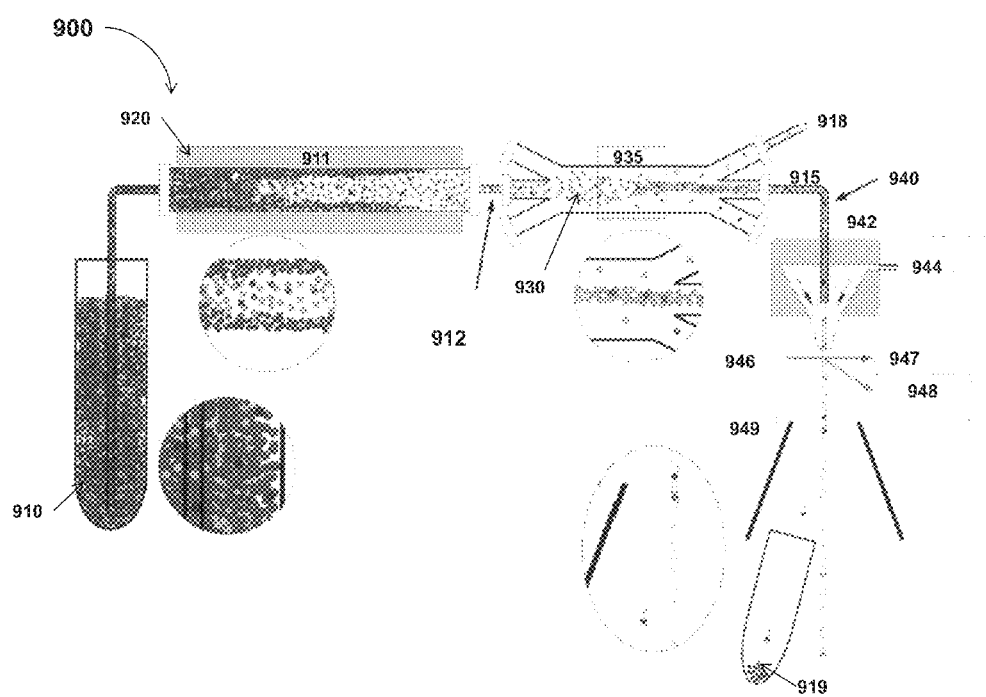
FIG. 9 is a diagram of a including a magnetic separation device 920, an acoustic concentrator 930, and a flow cytometer 940, used to sort a liquid sample 910 according to embodiments of the present disclosure. A magnetic reagent is added to a liquid sample 910 containing peripheral blood mononuclear cells (PBMCs) at a concentration of about $10^7$ cells/ml. The liquid sample 910 is flowed through a magnetic separation device 920 (e.g., at a flow rate of about 200-400 µl/min), which retains the cells of the liquid sample 910 that have been labeled with the magnetic reagent (e.g., red cells). The fluid that exits the magnetic separation device is thus enriched for CD4 T lymphocytes (e.g., at a concentration of about $2.5 \times 10^6$ cells/ml). This fluid is flowed through an acoustic concentrator 930, such as an acoustic concentrator of the type illustrated in FIG. 8, Panels A-D. The acoustic concentrator contains a piezoelectric transducer 935 (e.g., PZT) that, when activated, causes the CD4 T lymphocytes to move towards the pressure node formed in the center of the channel. This concentrated region is collected by the center washed sample outlet, which is fluidically coupled to a sorter 940, such as a BD Biosciences Influx™ cell sorter. Waste is removed through two outlets on the acoustic concentrator. The washed sample 915 has thus been enriched for CD4 T lymphocytes (e.g., at a concentration of about $10^7$ cells/ml) relative to the fluid that was flowed into the acoustic concentrator. Sorting the washed sample 915 using a flow cytometer 940 at an appropriate flow rate (e.g., at a flow rate of about 40-60 µL/min) may isolate the minor population of dark blue cells, which may be collected 919.

In certain aspects, the systems are flow cytometric systems that include a flow cytometric sample fluidic subsystem, as described below. In addition, the flow cytometric systems include a flow cytometer fluidically coupled to the flow cytometric sample fluidic subsystem. In certain aspects, a system includes a flow cytometric sample fluidic subsystem that includes a magnetic separation device (e.g., as described above) and an acoustic concentrator device (e.g., as described above) fluidically coupled to the magnetic separation device. Systems may include a flow cytometer (e.g., a BD Biosciences FACSCanto™ flow cytometer, a BD Biosciences Influx™ cell sorter, and the like) fluidically coupled to the flow cytometric sample fluidic subsystem. FIG. 9 presents a diagram of such a system 900, which includes a magnetic separation device 920 having magnetic field source 911, an acoustic concentrator 930 with piezoelectric acoustic transducer 935, and a flow cytometer 940. Illustrations of the mechanical components of systems of the present disclosure are shown in FIG. 10, panels A-B.

FIG. 9 illustrates an example of devices according to certain embodiments, where the device is in communication with sample 910 into the inlet of magnetic separator 920. The outlet of magnetic separator 920 is in fluid communication with conduit 912 having enriched cells (e.g., CD4 enriched T-lymphocytes) with acoustic concentrator 930. Acoustic concentrator 930 includes outlet conduit 915 to collect sample passing through acoustic separator 930. Fluidic sample at the outlet of acoustic separator 930 may be passed though to waste compartment 918. Fluidic sample at the outlet of acoustic separator 930 is collected through flow cytometer 940. Flow cytometer 940 includes a sorter flow cell 942 and sheath reservoir 944, excitation optics 946, deflection plates 949, front scatter detector(s) 947 and side scatter and fluorescence detector(s) 948. From flow cytometer 940, sorted sample 919 (e.g., enriched and sorted cells) is collected. The systems may generally include one or more subject fluidic devices as described herein and a processor configured to control the one or more fluidic devices. These components may be integrated into the same article of manufacture as a single unit, or distributed among two or more different units (e.g., as a system) where the two or more different units are in communication with each other, e.g., via a wired or wireless communication protocol.

Accordingly, aspects of the present disclosure further include systems, e.g., computer based systems, which are configured to manipulate components in a liquid sample as described above. A "computer-based system" refers to the hardware, software, and data storage devices used to analyze the information of the present invention. The minimum hardware of embodiments of the computer-based systems includes a central processing unit (CPU) (e.g., a processor), an input device, an output device, and data storage device. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing one or more tasks involved in the analysis of the magnetically labeled moieties. In certain embodiments, the system includes hardware, firmware, and/or software that visualizes the information of cell entrainment during sorting.

In certain aspects, a system may operate in a closed-loop fashion. For example, in some embodiments a system may measure one or more parameters of sorting, such as the observed electronic efficiency of a flow cytometer, the sample entrainment value, the position of cells in the sorting droplets, and the like. Examples of such parameters and monitoring software are provided in FIGS. 11-16. The system may change one or more parameters of the subject fluidic sorting devices on a substantially real-time basis to automatically obtain more efficient results and/or to optimize the processing rates depending on user requirements. For example, the system may alter one or more of the flow rate of a magnetic separation device, the flow rate of an acoustic separation device, the frequency of the vibration generator of an acoustic concentration device, the power applied to the vibration generator, etc. In certain aspects, such a closed-loop system may involve applying one or more statistical or learning machine algorithms, such as genetic algorithms, neural networks, hidden Markov models, Bayesian networks, and the like.

Additionally, systems of the present disclosure may include a number of additional components, such as data output devices, e.g., monitors, printers, and/or speakers, data input devices, e.g., interface ports, a keyboard, a mouse, etc., fluid handling components, power sources, etc.

Methods

Aspects of the present disclosure include methods of manipulating components of a fluid sample, such as by using devices and systems as described above. In certain embodiments, the method includes separating magnetically labeled moieties from non-magnetically labeled moieties in the sample, thereby creating a first sorted sample, and acoustically concentrating the first sorted sample to produce a second sorted sample. In certain aspects, the method further includes collecting the second sorted sample, and/or analyzing the sorted sample.

In certain instances, separating magnetically labeled moieties from non-magnetically labeled moieties in the sample includes applying a magnetic field having a magnetic flux sufficient to separate magnetically labeled moieties from non-magnetically labeled moieties in the sample. The magnetic field may be applied continuously as the sample flows through the conduit, or may be applied discontinuously in a pulsed application. In certain embodiments, the magnetic field source is a permanent magnet as described above, and thus the magnetic field is applied continuously to the sample as the sample flows through the conduit.

Aspects of the methods disclosed herein may include analyzing or assaying the sorted sample. Assay methods disclosed herein may be qualitative or quantitative. Thus, as used herein, the term "detection" or "separation" refers to both qualitative and quantitative determinations, and therefore includes "measuring" and "determining a level" of a component in a sample.

Aspects of the methods disclosed herein may further include attaching a magnetic label to one or more target moieties in a sample prior to performing the magnetic separation assay (e.g., prior to separating magnetically labeled moieties from non-magnetically labeled moieties in the sample). As such, the method may include magnetically labeling one or more moieties in a sample prior to performing the magnetic separation assay. Magnetic labels of interest may be retained by the device if they flow through a portion of a conduit in close proximity to the magnetic field produced by the device, e.g., between the magnetic field sources and/or between the magnetic field guides of the device).

Magnetic labels useful in the practice of certain embodiments of the present disclosure are magnetic particles, such as, but not limited to ferromagnetic, paramagnetic, super-paramagnetic, anti-ferromagnetic, or ferromagnetic particles. In certain instances, the magnetic particles appear "nonmagnetic" (e.g., have a remnant magnetization of substantially zero) in the absence of a magnetic field. Magnetic particles with a substantially zero remnant magnetization may not substantially agglomerate with each other in solution in the absence of an external magnetic field.

The magnetic particles may be chemically stable in a biological environment, which may facilitate their use in the assay conditions. In some cases, the magnetic particles are biocompatible, e.g., water soluble and functionalized so that they may be readily attached to biomolecules of interest, such as an antibody that specifically binds to a target analyte. By associating or binding magnetic particles to a specific antibody, the magnetic particles may be targeted to a specific analyte through the specific binding interactions between the antibody and complementary antigen. In some instances, the magnetic label may be bound to the protein or antibody as described above through a non-covalent or a covalent bond with each other. Examples of non-covalent associations include non-specific adsorption, binding based on electrostatic (e.g., ion, ion pair interactions), hydrophobic interactions, hydrogen bonding interactions, specific binding through a specific binding pair member covalently attached to the surface of the magnetic particle, and the like. Examples of covalent binding include covalent bonds formed between the biomolecule and a functional group present on the surface of the magnetic particle, e.g. —OH, where the functional group may be naturally occurring or present as a member of an introduced linking group.

In certain embodiments, the magnetic particles are nanoparticles. By "nanoparticle" is meant a particle having an average size (e.g., mean diameter) in the range of 1 nm to 1000 nm. In certain embodiments, the average size (e.g., mean diameter) of the magnetic nanoparticles is sub-micron sized, e.g., from 1 nm to 1000 nm, or from 1 nm to 500 nm, or from 5 nm to 250 nm, such as from 5 nm to 150 nm, including from 5 nm to 50 nm. For example, magnetic nanoparticles having a mean diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, 150 nm, and 200 nm as well as nanoparticles having mean diameters in ranges between any two of these values, are suitable for use herein. In certain embodiments, the magnetic particles are substantially uniform in shape. For example, the magnetic particles may be spherical in shape. In addition to a spherical shape, magnetic nanoparticles suitable for use herein can be shaped as disks, rods, coils, fibers, pyramids, and the like.

The magnetic label may be stably associated with the moiety (or moieties) of interest through non-covalent or covalent interactions as described above. For example, the magnetic label may be associated with the moiety of interest through a binding interaction between a binding pair of molecules. The binding pair of molecules may vary depending on the binding interaction of interest. Binding interactions of interest include any interaction between the binding pair of molecules, where the binding interaction occurs with specificity between the binding pair of molecules under the environmental conditions of the binding interaction. Examples of binding interactions of interest include, but are not limited to: nucleic acid hybridization interactions, protein-protein interactions, protein-nucleic acid interactions, enzyme-substrate interactions and receptor-ligand interactions, e.g., antibody-antigen interactions and receptor-agonist or antagonist interactions.

Examples of molecules that have molecular binding interactions of interest include, but are not limited to: biopolymers and small molecules, which may be organic or inorganic small molecules. A "biopolymer" is a polymer of one or more types of repeating units. Biopolymers may be found in biological systems (although they may be made synthetically) and may include peptides, polynucleotides, and polysaccharides, as well as such compounds composed of or containing amino acid analogs or non-amino acid groups, or nucleotide analogs or non-nucleotide groups. As such, biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. For example, a "biopolymer" may include DNA (including cDNA), RNA, oligonucleotides, PNA, other polynucleotides, and the like. A "biomonomer" references a single unit, which can be linked with the same or other biomonomers to form a biopolymer (e.g., a single amino acid or nucleotide with two linking groups, one or both of which may have removable protecting groups).

In some instances, the binding pair of molecules are ligands and receptors, where a given receptor or ligand may or may not be a biopolymer. The term "ligand" as used herein refers to a moiety that is capable of covalently or otherwise chemically binding a compound of interest. Ligands may be naturally-occurring or manmade. Examples of ligands include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, proteins, and the like. The term "receptor" as used herein is a moiety that has an affinity for a ligand. Receptors may be attached, covalently or non-covalently, to a binding member, either directly or via a specific binding substance. Examples of receptors include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, organelles, and the like. A "ligand receptor pair" is formed when two molecules have combined through molecular recognition to form a complex.

Accordingly, the methods may include detecting a binding interaction between a binding pair of molecules. The binding interaction may include one member of the binding pair of molecules that is labeled with a magnetic label as described herein. For example, one member of the binding pair of molecules may be magnetically labeled and may bind to its complementary binding pair member to form a binding pair complex. The binding pair complex may be separated from the moieties not of interest in the sample using a magnetic separation device and methods as described herein. After performing the magnetic separation assay, the binding pair complex may be detected using any convenient method, such as, but not limited to, flow cytometry, fluorescence detection, high-performance liquid chromatography (HPLC), electrophoresis, combinations thereof, and the like.

Aspects of methods of the present disclosure may further include analyzing the sorted sample. In some instances, the analyzing includes further sorting the sample. For instance, the method may include counting and/or sorting the sample using a flow cytometry device. Flow cytometric assay procedures are well known in the art. See, e.g., Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. January; 49(pt 1):17-28; Linden, et. al., *Semin Throm Hemost.* 2004 October; 30(5):502-11; Alison, et al. *J Pathol*, 2010 December; 222(4):335-344; and Herbig, et al. (2007) *Crit Rev Ther Drug Carrier Syst*. 24(3):203-255; the disclosures of which are incorporated herein by reference.

In certain embodiments, the sample is not analyzed at any time during methods of the invention. As such, in these embodiments, the sample is not visualized or otherwise characterized during either sample enrichment in the magnetic separation device or the acoustic concentrator device. In these embodiments, the sample is flowed through each of the magnetic separation device and the acoustic concentrator device without any separate step for visualizing, characterizing or otherwise determining the composition of the enriched sample. For example, the sample is not analyzed during methods of the invention by any optical characterization protocols such as visualization with the naked eye or by fluorescence, UV-vis, infrared or light scattering spectroscopy.

In certain aspects, the methods of the present disclosure may increase the speed of sorting the sample on a device (e.g., a flow cytometry device) relative to the speed of sorting on the device in the absence of performing methods of the present disclosure. The speed of sorting may be increased by 2 fold or more, such as 4 fold or more, including 5 fold or more, or 10 fold or more.

In certain aspects, the methods of the present disclosure may increase the electronic efficiency of a device (e.g., a flow cytometry device) relative to the electronic efficiency of the device in the absence of performing methods of the present disclosure. The electronic efficiency may be increased by 1% or more, such as 2% or more, including 5% or more, or 10% or more.

In certain aspects, the methods of the present disclosure may increase the sort efficiency of a device (e.g., a flow cytometry device) relative to the sort efficiency of the device in the absence of performing methods of the present disclosure. The sort efficiency may be increased by 1% or more, such as 2% or more, including 5% or more, or 10% or more.

In certain aspects, the methods of the present disclosure may increase the entrainment of a sample on a device (e.g., a flow cytometry device) relative to the entrainment on the device in the absence of performing methods of the present disclosure. The entrainment may be reduced by 2 fold or more, such as 4 fold or more, including 5 fold or more, or 10 fold or more.

In certain cases, analyzing the sorted sample includes determining one or more physical and/or chemical properties of the components of the sample, such as, but not limited to, fluorescence, mass, charge, chemical composition, UV absorption, infrared absorption, light scattering, combinations thereof, and the like.

Kits

Also provided are kits for practicing one or more embodiments of the above-described methods. The subject kits may include various components and reagents. In some instances, the kits include at least reagents finding use in the methods (e.g., as described above), such as a wash solution or buffer for washing a reusable conduit, and one or more magnetic labels for labeling moieties in a sample, such that magnetically labeled moieties may be separated from non-magnetically labeled moieties in the sample.

In some instances, the kits include at least reagents finding use in the methods (e.g., as described above); and a computer readable medium having a computer program stored thereon, wherein the computer program, when loaded into a computer, operates the computer to perform a flow cytometric assay as described herein; and a physical substrate having an address from which to obtain the computer program.

In addition to the above components, the subject kits may further include instructions for practicing the methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, flash memory, etc., on which the information has been recorded. Yet another means that may be present is a website address which may be used via the Internet to access the information at a removed site. Any convenient means may be present in the kits.

Utility

The subject devices, systems, methods, and kits find use in a variety of different applications where it is desirable to sort and/or concentrate components (e.g., cells) in a liquid sample.

For example, embodiments of the subject methods and devices may facilitate the sorting of a liquid sample comprising cells. In FIG. 9, for example, a device of embodiments of the present disclosure is used to perform a method of embodiments of the present disclosure, wherein a relatively small population of cells (e.g., CD4 T lymphocytes) are sorted from a sample containing a majority of cells that are not CD4 T lymphocytes. Using methods and/or devices of the present disclosure, these cells may be separated from the liquid sample at high efficiency, high flow rate and low cost.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Materials and Methods

The following are general materials and protocols used in Examples below.

Magnetic Separation Device

The magnetic separation device included six permanent magnets (N45 rare earth Neodymium (NdFeB) bar magnet, 2 in.×0.5 in.×0.5 in., CMS Magnetics, Inc.) and six wedge-shaped magnetic field guides. The magnetic field guides were made of stainless steel and had a 60 degree apex angle. The apex edges of each magnetic field guides had linear profiles. The six permanent magnets were arranged into two sets of three magnets. Each set of three magnets had overall dimensions of 6 in.×0.5 in.×0.5 in. The first and second sets of magnets were positioned directly opposite from each other in the device. Each permanent magnet had a corresponding magnetic field guide attached, and the apex edges of the first set of magnetic field guides were directly opposite and parallel to the apex edges of the second set of magnetic field guides. The gap between the apex edges of the two sets of magnetic field guides was 1 mm. The magnetic flux density in the gap between the apex edges of the magnetic field guides was measured to be 1.1 Tesla and the magnetic field gradient was 0.8 T/mm. The magnetic flux was localized in the gap between the apex edges of the magnetic field guides with a direction going from the first set of magnets to the second set of magnets.

Conduit

The conduit was PTFE (Polytetrafluoroethylene) tubing with a 2 mm outer diameter and a 1 mm inner diameter. The effective length of the conduit was 6 inches, which corresponds to the length of the set of magnets in contact with the conduit.

Acoustic Concentrator Device

The acoustic concentrator device was designed and manufactured largely as described in U.S. Pat. No. 6,929,750; Laurell, et al. (2007) Chem. Soc. Rev., 2007, 36, 492-506; Petersson, et al. (2005) Analytical Chemistry 77: 1216-1221; and Augustsson, et al. (2009) Lab on a Chip 9: 810-818; the disclosures of which are incorporated herein by reference. Briefly, the acoustic concentrator device included a chip microfabricated in silicon using conventional anisotropic wet etching. The rectangular cross-section main channel was 125 µm deep, 350 µm wide, and 30 mm long. At the beginning of the main channel, there was one center inlet channel and two side inlet channels. The side inlet channels originated from a common inlet. At the end of the main channel there was one center outlet channel and two side outlet channels with a common outlet (FIG. 8, Panel D). The channels were sealed by anodic bonding of a glass lid. Tubing and a piezoceramic plate were attached to the backside of the chip. The flow rates through the inlets and outlets were controlled using syringe pumps. The total volumetric flow through the main channel was 0.3-2.0 µl/sec or lower, resulting in a Reynolds number below 20, i.e., a truly laminar flow. The main channel was actuated via a piezoceramic plate operated at 2 MHz, corresponding to its fundamental resonance mode. The activation voltage was initially set at 10 Vpp.

Reagents and Samples

BD Imag™ Human CD4 T Lymphocyte Enrichment Set (Becton, Dickinson and Co.) that included biotin human CD4 T lymphocyte enrichment assay mixture and streptavidin coated magnetic particles was used in the experiments. The magnetic particles were superparamagnetic particles having an average diameter ranging from 200 nm to 400 nm and a stock concentration of 200 µg/ml. According to the manufacturer's recommended protocol, 5 µl of the cocktail was used per million cells. After incubation and washing, 5 µl streptavidin coated magnetic particles was used per million cells. The experimental sample was human peripheral blood mononuclear cells (PBMCs) prepared by using BD Vacutainer® CPT™ Cell Preparation Tube with Sodium Citrate (Becton, Dickinson and Co.). The PBMCs were suspended in 1× phosphate buffered saline (PBS) with 0.5% bovine serum albumin (BSA) and 20 mM EDTA in a concentration of 2 to 50 million cells per ml. Biotinylated antibodies in the assay mixture bound to all populations in PBMCs except CD4+ T lymphocytes. Streptavidin that was conjugated to magnetic particles in the assay mixture bound to biotin specifically. With the above two step binding method, all cells in PBMCs except CD4+ T lymphocytes were magnetically labeled by the specific binding interaction between the biotin labeled PBMCs and the streptavidin coated magnetic particles.

The sample was flowed through the conduit positioned in between the magnetic field guides in a magnetic separation device and magnetically labeled cells were captured in the magnetic field in the gap between the apex edges of the magnetic field guides. The CD4+ T lymphocytes, which were not magnetically labeled, were not retained in the conduit and passed through the conduit to an acoustic concentrator device positioned downstream from the magnets.

Operation Conditions

Magnetically labeled cells and non-labeled cells passed through the magnetic separation device in a conduit driven by a peristaltic pump or air pressure. The flow rate was 200 µl/min to 400 µl/min. For example, an air compressor was used to apply 18 psi to the sample in the conduit to achieve a 400 µl/min flow rate in the conduit. The flow rate in the acoustic concentrator was controlled by the flow rate of the conduit and the syringe pumps of the acoustic concentrator to achieve a volumetric flow through the main channel of about 0.3-2.0 µl/sec, or lower. Optionally, the flow rates of the acoustic concentrator device may be adjusted to achieve the degree of concentration desired and optimal flow for a sorter (e.g., such as a BD Biosciences Influx™ cell sorter).

Experiments were performed at room temperature. Optionally, the labeled PBMCs were kept on ice before performing the separation assay.

Flow Cytometric Analysis

Flow cytometric sorting was performed on a BD Biosciences Influx™ cell sorter, according to the manufacturer's instructions. Software analyses were performed using the BD Influx Sort Analysis tool and BD FACS Optimizer tool.

Example 1

Figure 15:
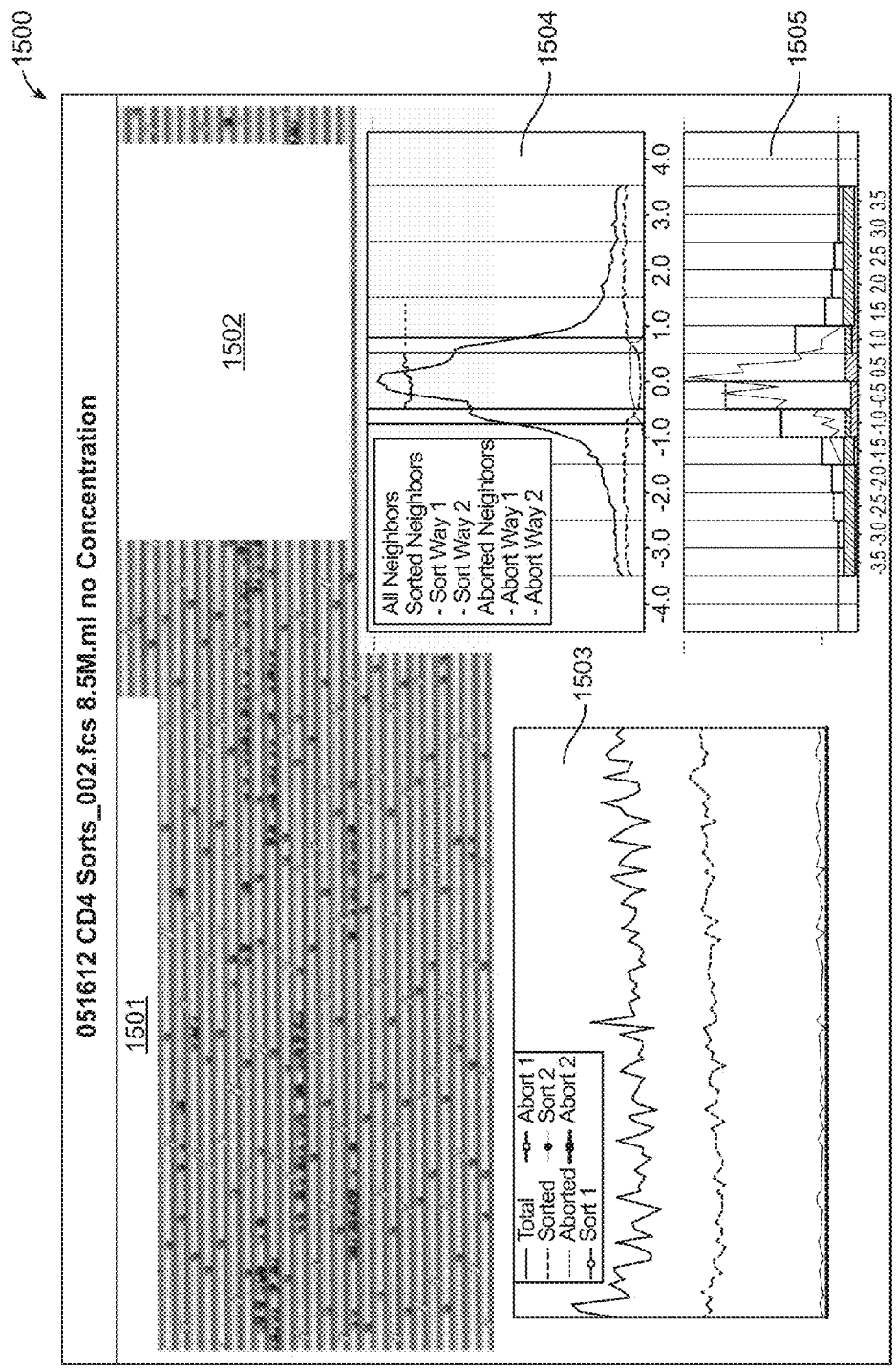
FIG. 15 is a graphical depiction of the position of cells in sorting droplets for a sample that was not prepared with systems of the present disclosure. This analysis was conducted using the BD Influx Sort Analysis Tool. This sample exhibits a high entrainment factor (47), and several clumps of cells can be seen. The observed electronic efficiency (91.7%) was lower than the expected value (98.4%).
Figure 16:
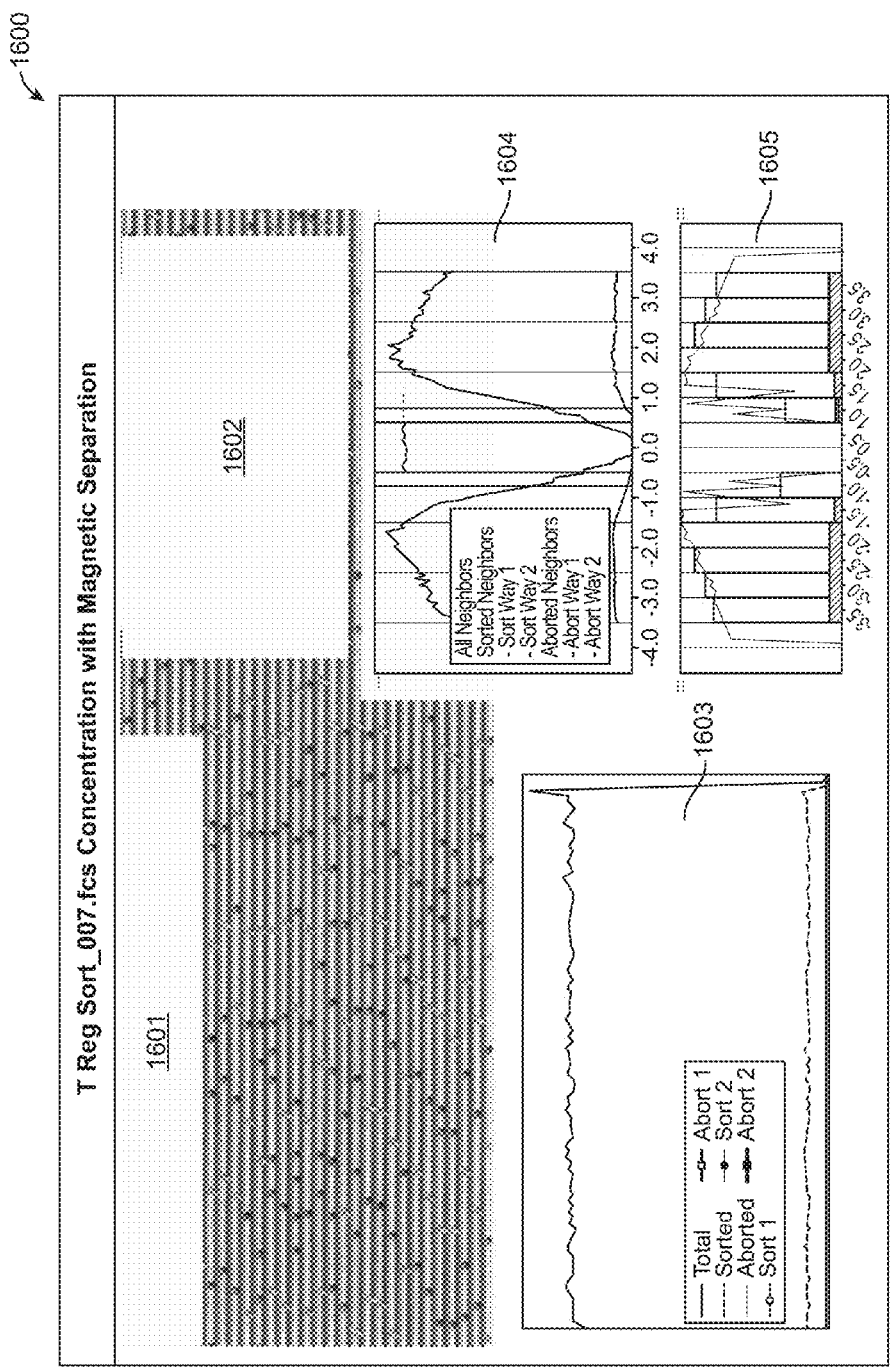
FIG. 16 is a graphical depiction of the position of cells in sorting droplet, for a sample that was prepared with systems of the present disclosure. In contrast to the sample shown in FIG. 15, the sample exhibited a low entrainment factor (0.02), and no clumps of cells were seen. The observed electronic efficiency (100%) was better than the expected value (96.7%). This analysis was conducted using the BD Influx Sort Analysis Tool.

Higher than expected electronic and sort efficiencies were observed for samples processed by a pre-enrichment system that included the magnetic separation device and acoustic concentrator device (FIGS. 15-16).

Cells in real world biological samples often aggregate and these aggregates cannot be efficiently detected or sorted. Their presence often affects the drop breakoff behavior of neighboring drops further reducing sort efficiency. Very well behaved samples will exhibit Poisson distribution and the electronic efficiency of the detection and sorting efficiency can be predicted statistically. The metric entrainment factor has been developed to quantitatively describe how much a population of cells deviates from the normal Poisson distribution. A sample with an entrainment factor of 1 would exhibit a normal Poisson distribution whereas aggregated samples often exhibit values of 8-10, or higher.

Figure 11:
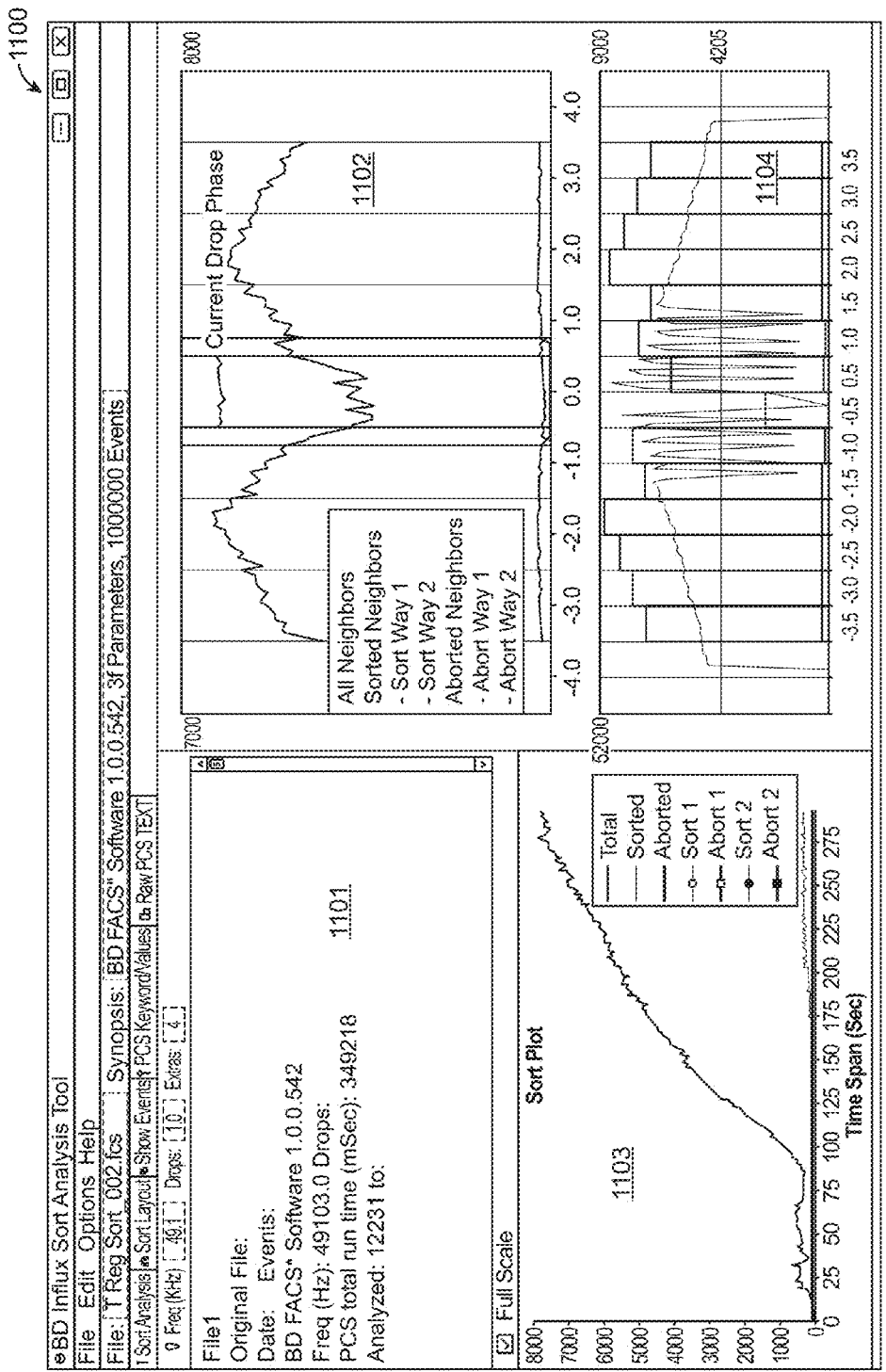
FIGS. 11-12 show screen captures of software used to measure the sorting efficiency of systems of the present disclosure. The BD Influx Sort Analysis Tool was used to compare the efficiencies of sorting on a flow cytometer either with or without the use of the subject devices. The software was used determine observed versus expected electronic efficiency. Expected results were based on a sample exhibiting normal Poisson distribution. Sample entrainment—a measure of the degree of aggregation of the cells in a sample, defined as the ratio of the observed distribution of the cells over the expected distribution based on a normal Poisson distribution—was also calculated. Samples exhibiting a normal Poisson distribution have an entrainment factor of 1, highly aggregated samples >1, and better than Poisson <1. The software also provides information on event rate versus time and an analysis of the position of cells in adjacent drop bins.
Figure 12:
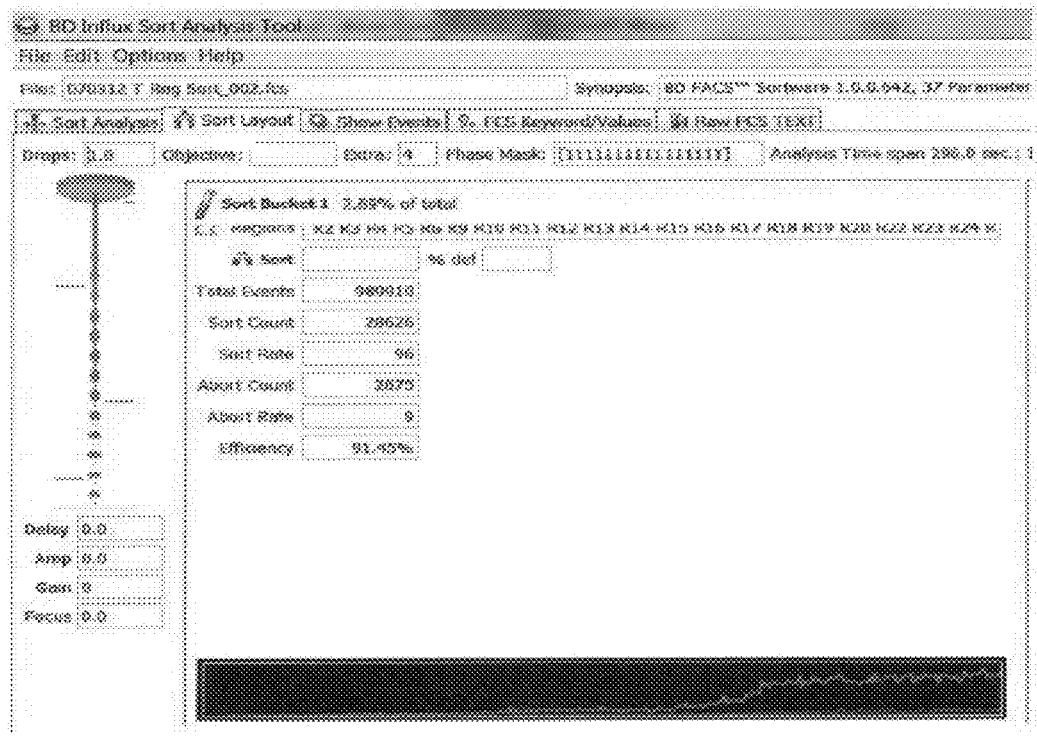

FIGS. 11-12 show screen captures of software from the BD Influx Sort Analysis Tool used to measure the sorting efficiency of systems of the present disclosure. FIG. 11 depicts a screen capture of data analysis panel 1100 used determine observed versus expected electronic efficiency. Data analysis panel 1100 includes data report 1101. The BD Influx Sort Analysis Tool also includes graphical representations 1102, 1103 and 1104 of the data. Expected results were based on a sample exhibiting normal Poisson distribution. Sample entrainment—a measure of the degree of aggregation of the cells in a sample, defined as the ratio of the observed distribution of the cells over the expected distribution based on a normal Poisson distribution—was also calculated. Samples exhibiting a normal Poisson distribution have an entrainment factor of 1, highly aggregated samples >1, and better than Poisson <1. The software also provides information on event rate versus time and an analysis of the position of cells in adjacent drop bins.

Figure 13:
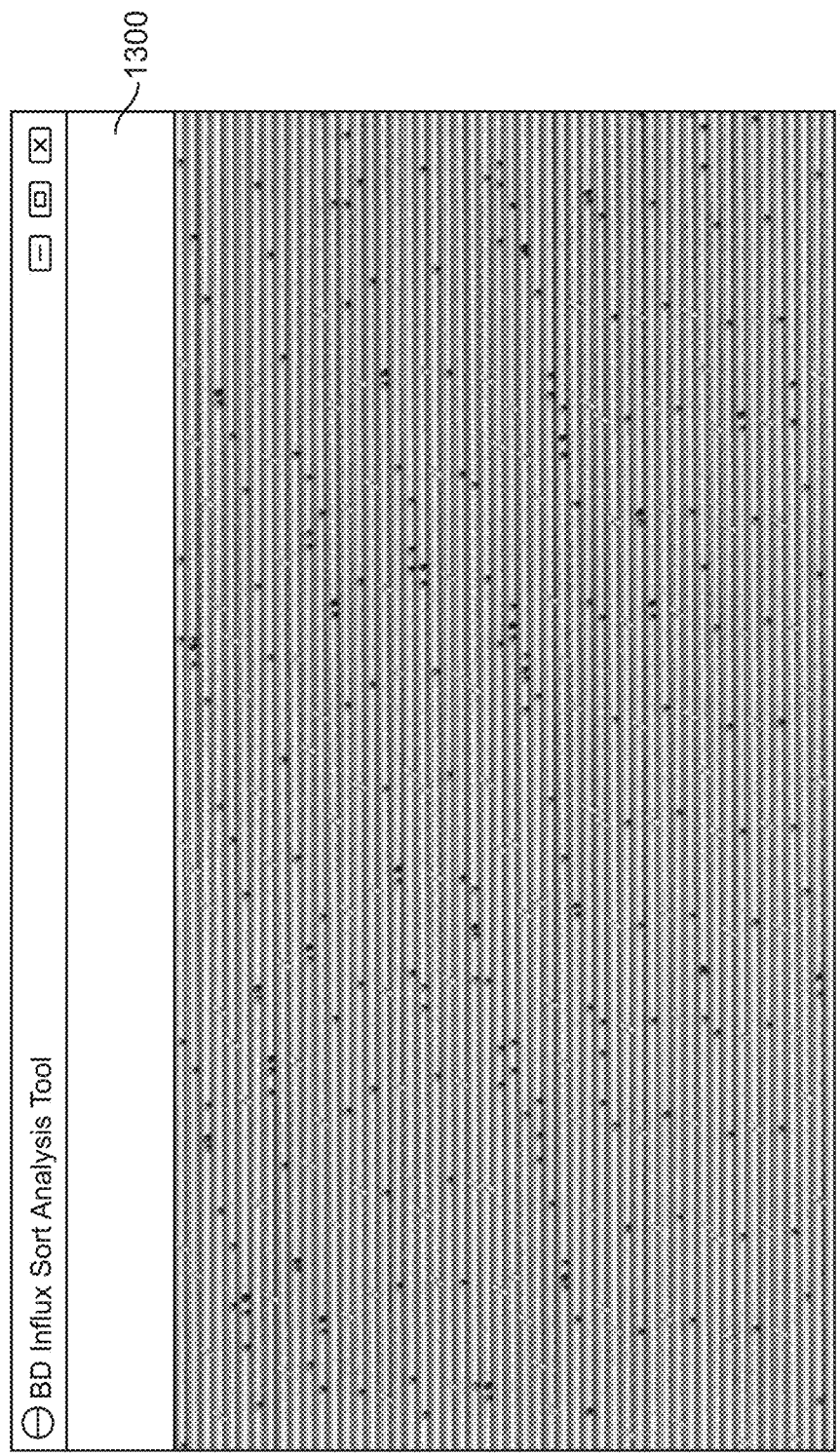
FIG. 13 is a screen capture of BD Influx Sort Analysis Tool software used to measure the sorting efficiency of systems of the present disclosure, showing a graphical depiction of the position of cells in the sorting droplets.

FIG. 13 is a screen capture 1300 of BD Influx Sort Analysis Tool software used to measure the sorting efficiency of systems of the present disclosure, showing a graphical depiction of the position of cells in the sorting droplets.

Figure 14:
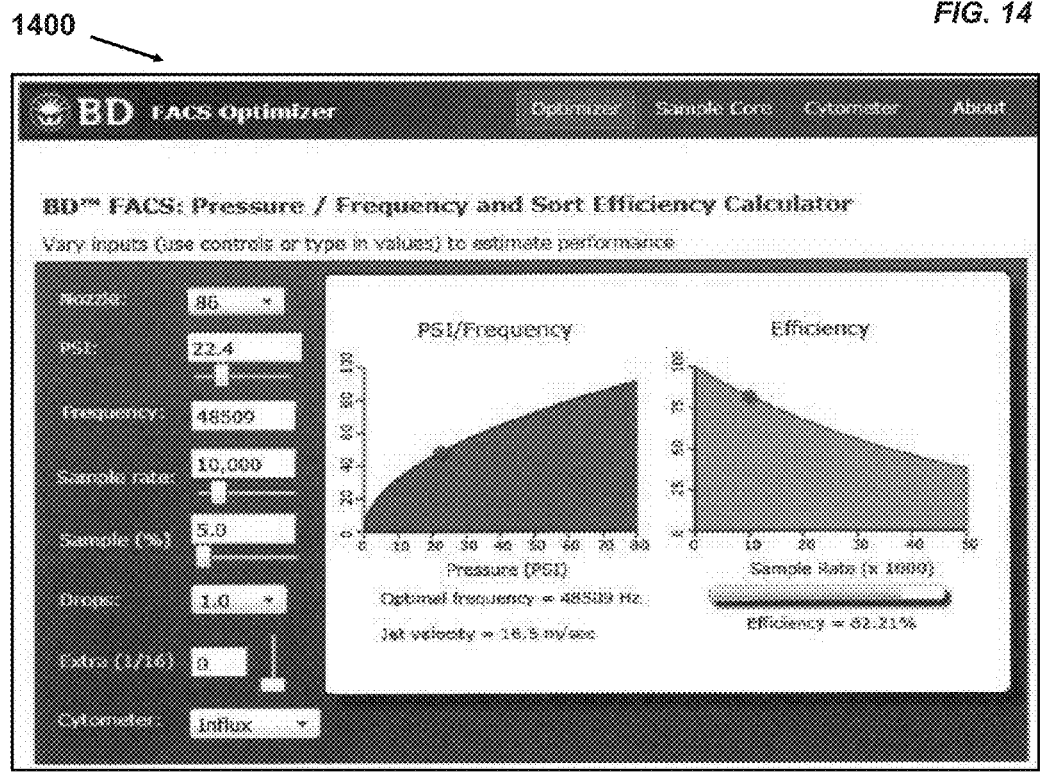
FIG. 14 is a screen capture of software (BD FACS Optimizer) that was used to establish sorting conditions and to predict sort efficiencies. The software was used to predict sort efficiencies, which were then compared to observed efficiencies for samples prepared with or without the use of devices of the present disclosure.

FIG. 14 is a screen capture 1400 of software (BD FACS Optimizer) that was used to establish sorting conditions and to predict sort efficiencies. The software was used to predict sort efficiencies, which were then compared to observed efficiencies for samples prepared with or without the use of devices of the present disclosure.

Samples processed using magnetic separation and acoustic concentration exhibited entrainment factors of 0.02 to 0.4, which demonstrated that the process forces the ordering of the cells into a more regular distribution. This is a desirable result and increases can be measured in electronic and sort efficiencies, which translate into faster sorting procedures which produce cellular products with better biological function. For example, FIG. 15 presents screen capture 1500 of BD Influx Sort Analysis Tool software in which a sample was not prepared with systems of the present disclosure. This sample exhibits a high entrainment factor (47), and several clumps of cells can be seen. Graphical depiction 1501 illustrates that clumps of cells can be seen in this sample and entrainment is high. Data panel 1502 provides parameters of the data:

Event rate=3000;
Sort rate=1721;
Abort rate=65;
Sort efficiency=96.3%-96.6%;
Entrainment=47
Electronic Efficiency=91.7 (observed)-98.4% (expected)

Here, the observed electronic efficiency (91.7%) was lower than the expected value (98.4%). The BD Influx Sort Analysis Tool also includes graphical representations 1503, 1504 and 1505 of the data.

FIG. 16 presents screen capture 1600 of BD Influx Sort Analysis Tool software of a sample processed using magnetic separation and acoustic concentration according to embodiments of the present invention prior to sorting. Graphical depiction 1601 illustrates that sample running at 12M/mL after magnetic separation and concentration provided a sort and electronic efficiency better than expected. Data panel 1602 provides data output:

Event rate=7000;
Sort rate=553;
Abort rate=7;
Sort efficiency=98.7%-85.4%;
Entrainment=0.02
Electronic Efficiency=100% (observed)-96.7% (expected)

Here, the sample exhibited a low entrainment factor (0.02), and no clumps of cells were seen. The observed electronic efficiency (100%) was better than the expected value (96.7%). The BD Influx Sort Analysis Tool also includes graphical representations 1603, 1604 and 1605 of the data.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of sorting a liquid sample comprising cells or particles, the method comprising:
   a) seperating magnetically labeled cells or particles from non-magnetically labeled cells or particles in the sample, by introducing the sample into a sorting device comprising a magnet that separates the magnetically labeled cells or particles from the non-magnetically labeled cells or particles, thereby creating a first sorted sample; and
   b) acoustically concentrating the first sorted sample to produce a second sorted sample by exposing the first sorted sample to acoustic waves generated by an acoustic concentrator, wherein the magnet and the acoustic concentrator are spatially seperated in the device.

2. The method according to claim 1, comprising collecting the second sorted sample.

3. The method according to claim 1, comprising analyzing the second sorted sample.

4. The method according to claim 3, wherein analyzing the second sorted sample comprises flow cytometric analysis.

5. The method according to claim 1, wherein the second sorted sample has an entrainment factor of about 0.0 to 1.0.

6. The method according to claim 1, further comprising labeling the cells or particles in the liquid sample with a magnetic label before the separating step.

7. The method according to claim 1, wherein the method is controlled by a processor.

8. The method according to claim 1, wherein the processor controls the method under a closed-loop feedback mechanism.

9. The method according to claim 1, wherein the liquid sample comprises a biological sample.

10. The method according to claim 1, wherein the liquid sample is obtained from a human.

* * * * *